(12) United States Patent
Kumar

(10) Patent No.: US 6,310,048 B1
(45) Date of Patent: Oct. 30, 2001

(54) ANTISENSE MODULATION OF AMYLOID BETA PROTEIN EXPRESSION

(75) Inventor: Vijaya B. Kumar, Ellisville, MO (US)

(73) Assignee: St. Louis University, St. Louis, MO (US)

( * ) Notice: Subject to any disclaimer, the term of this patent is extended or adjusted under 35 U.S.C. 154(b) by 0 days.

(21) Appl. No.: 09/458,481

(22) Filed: Dec. 9, 1999

(51) Int. Cl.$^7$ ............... A61K 48/00; C07H 21/04; C07H 21/02; C12N 15/85; C12N 15/86

(52) U.S. Cl. ............... 514/44; 435/6; 435/91.1; 435/325; 435/375; 536/23.1; 536/24.5; 536/24.3; 536/24.31; 536/34.33

(58) Field of Search ............... 435/6, 91.1, 91.3, 435/375, 325; 536/23.1, 23.2, 24.5, 24.3, 24.33, 24.31; 514/44

(56) References Cited

U.S. PATENT DOCUMENTS

| | | |
|---|---|---|
| 5,220,013 | 6/1993 | Ponte et al. . |
| 5,455,169 | 10/1995 | Mullan . |
| 5,643,726 | 7/1997 | Tanzi et al. . |
| 5,795,963 | 8/1998 | Mullan . |
| 5,801,154 * | 9/1998 | Baracchini ............... 514/44 |
| 5,837,449 | 11/1998 | Monia et al. . |
| 5,840,294 | 11/1998 | Kisilevsky et al. . |
| 5,851,787 | 12/1998 | Wasco et al. . |
| 5,853,985 | 12/1998 | Salbaum et al. . |
| 5,877,015 | 3/1999 | Hardy et al. . |
| 5,891,991 | 4/1999 | Wasco et al. . |

FOREIGN PATENT DOCUMENTS

WO88/03951   6/1988   (WO) .

OTHER PUBLICATIONS

Coulson et al., Down Regulation of the Amyloid protein precursor of Alzheimer's disease by antisense oligonucleotides reduces neuronal adhesion to specific substrata, Brain Research, 770, pp. 72–80, 1997.*

Crooke, Antisense Research and Application, Springer, New York, p. 1–50, Jul. 1998.*

Agrawal, "Antisense Oligonucleotides: towards clinical trials", TIBTech, vol. 14, pp. 376–387, Oct. 1996.*

Branch, "A good antisense molecule is hard to find", TIBS 23, pp. 45–50, Feb. 1998.*

Kumar et al., Anti–sense oligonucleotides to amyloid precursor protein restore acquisition and retention in senescence acclerated mouse (SAM P8), J. Investigative Medicine, vol. 45, No. 7, p. 325A, Sep. 1997.*

Gabuzda et al., Journal of Neurochemistry, pp. 2326–2329, Inhibition of β–Amyloid Production by Activation of Protein Kinase C, vol. 61, No. 6, 1993.

(List continued on next page.)

Primary Examiner—Robert A. Schwartzman
Assistant Examiner—Karen A. Lacourciere
(74) Attorney, Agent, or Firm—Howell & Haferkamp, L.C.

(57) ABSTRACT

An antisense compound comprising nucleotides complementary to a nucleic acid sequence coding for amyloid precursor protein (APP), wherein the antisense compound inhibits the expression of an amyloid beta protein (AβP) portion of the amyloid precursor protein coding sequence while permitting the expression of at least a portion of the amyloid precursor protein polynucleotide 5' to the AβP portion of the amyloid precursor protein coding sequence. Pharmaceutical compositions and formulations containing the compound and methods of using the compound to regulate AβP expression in cells and tissues and to treat disease are also provided.

25 Claims, 12 Drawing Sheets

OTHER PUBLICATIONS

Hsiao et al., Science, vol. 274, pp. 99–102, Correlative Memory Deficits, Aβ Elevation, and Amyloid Plaques in Transgenic Mice, Oct. 4, 1996.

Marshall et al., Science, vol. 259, pp. 1564–1570, Phosphorodithioate DNA as a Potential Therapeutic Drug, Mar. 12, 1993.

Suzuki et al., Science, vol. 264, pp. 1336–1340, An Increased Percentage of Long Amyloid β Protein Secreted by Familial Amyloid β Protein Precursor (βAPP$_{717}$) Mutants, May 27, 1994.

Volloch, FEBS Letters 390, pp. 124–128, A mechanism for β–amyloid overproduction in Alzheimer's disease: precursor–independent generation of β–amyloid via antisense RNA–primed mRNA synthesis, 1996.

Wagner, Nature, vol. 372, Gene inhibition using antisense oligodeoxynucleotides, Nov. 24, 1994.

Zaid et al., The Journal of Biological Chemistry, vol. 269, No. 39, p. 24007–13, Amyloid Precursor Protein mRNA Stability Is Controlled by a 29–Base Element in the 3'–Untranslated Region, Sep. 30, 1994.

* cited by examiner

```
M   L   P   S   L   A   L   L   L   L       A   A   W   T   V   R   A       L   E   V       P   T   D       G   N   A   G
ATG CTG CCCA GCT TGG CACT GCT CCT GCT G     GCC GCC CTG GA  CGG TTC GGGC     TCT GAG GTA     CCC ACT GAT G   GCA ACG CCGG

L   L   A       E   P   Q   I   A   M   F       C   G   K   L   N   M   H   M   N   V       Q   N   G       K   W   E
GCT GCT GGCA    GAA CCC AGA TCG CCA TGT TT      CTG TGG TAAA CTC AAC ATG C   ACA TGA ATGT    GCA GAA TGA    AAG TGG GAGT

S   D   P   S       G   T   K   T   C   I       G   T   K   E       G   I   L       Q   Y   C       Q   E   V   Y       P   E   L
CAG ATC ACCGT C     AGG GAC CAA ACCT GCA TTG     GCA CCA AGGA        GGG CAT CTG     CAG TAC TGCC    AAG AGG TCTA        CCC TGA ACTG

Q   I   T       N   V   V   E       A   N   Q   P   V   T       I   Q   N   W   C   K   R   G   R   K       Q   C   K   T
CAG ATC ACAA    AGT GGT GGA         AGC CAA CCA G  CCA GTG ACCA       TCC AGA ACTG GTG CAA GCG G   GCC GCA AGC           AGT GCA AGAC

H   T   H       I   V   I       P   Y   R   C       L   V   G       E   F   V       S   D   A   L   L   V   P       D   K   C
ACA CAC CCAC    ATC GTG ATTC     CTT ACC GTT G      GTG AGT TGT      GAG TTT GTGA    GCG ACG CCC T   TCT CGT GCCC        GAC AAG TGCA

K   F   L   H       Q   E   R       M   D   V       C   E   T   H       L   H   W       H   T   V       A   K   E   T       C   S   E
AGT TCC TAC A       CCA GGA GCGG    ATG GAT GTTT    GTG AGA CCCA       TCT TCA CTGG   CAC ACC GTCG    CCA AAA GAG AC       ATG CAG CGAG

K   S   T       N   L   H   D       Y   G   M       L   L   P       C   G   I   D       K   F   R       G   V   E       F   V   C   C
AAG AGC ACTA    ACT TGC ACGA        CTA TGG CATG    CTG CTG CCCT     TGC GGC ATC GA    CAA GTT CCGA    GGG GTA GAGT      TTG TAT GCTG

P   L   A       E   E   S       D   S   V   D       S   A   D       A   E   E       D   D   S   D       V   W   W       G   G   A
CCC GTT GCC     GAG GAA AGCG    ACA GCC GTG A       TTC TGC GGAT     GCA GAG AGAG     ATG ACT CTGA     TGT CTC TGT GG     GGT GGA GCGG

D   T   D   Y       A   D   G       G   E   D       K   V   V   E       V   A   E       B   E   E       V   A   D   V       E   E   E
ACA CAG ACTA        CGC TGA TGCC    GGT GAA GACA    AGT AGT AGA       AGT CGC CGAA     GAG GAG GAAG    TGG CTG ATGT       TGA GGA AGAG

E   A   D       D   D   E   D       V   E   D       G   D   E       V   E   E   E       A   E   E       P   Y   E       E   A   T   E
GAA GCT GATG    ATG ATG AGGA        TGT GGA GGAT     GGG GAC GAG     TGG AGG AGGA     GGC CGA GGAG    CCC TAC GAAG       AGG CCA CCGA

R   T   T       S   T   A       T   T   T   T       T   E   S       V   E   E       V   V   R   V   P       T   T   A
GAG AAC AACC    AGC ACT GCCA        CCA CCA CCACT    ACT GAG TCG     GTG GAG GAG     GTG GTC CGT GGT   AGG AGG TGT GT   CCG AGT TCCC   ACG ACA GCAG

A   S   T   P       D   A   A       D   K   Y       L   E   T   P       G   D   E       N   E   H       A   H   F   Q       K   A   K
GCA ACA ACC         CCA GCA CCGCC   CGA CGC CGCC    GAC AAG TAC C    TGG AGA CACC     CGG GGA CGAG    AAC GAC GAT G     CCC ATT CCA      GAA AGC CAAA

E   R   L       E   A   K   H       R   E   R       M   S   Q       V   M   R   E       W   E   E       A   E   R       Q   A   K   N
GAG AGG CTGG    AAG CCA AGCA       CCG AGA GAGA     ATG TCC CAGG    GTG ATG AGAGA    TGG GAA GAG     GCA GAG CGT C    AAG CCA AGAA
```

FIGURE 3A

```
L   P   K   A   D   K   K   A   V   I   Q   H   F   Q   E   K   V   E   S   L   E   Q   E   A   A   N
CTTGCCCAAA GCTGACAAGA AGGCCGTTAT CCAGCATTTC CAGGAGAAAG TGGAATCTCT GGAACAGGAA GCAGCCAATG

E   R   Q   Q   L   V   E   T   H   M   A   R   V   E   A   M   L   N   D   R   R   R   L   A   L   E   N
AGAGACAGCA GCTTGTAGAG ACACACATGG CCAGAGTTGA AGCCATGCTC AATGACCGCC GCCGCCTGGC CCTCGAGAAT

Y   I   T   A   L   Q   A   V   P   P   H   V   F   N   M   L   K   K   Y   V   R   A   E   Q
TACATCACTG CACTGCAGGC GGTGCCCCCA AGGCCTCATC ATGTGTTCAA CATGCTGAAG AAGTACGTCC GTGCGGAGCA

K   D   R   Q   H   T   L   K   H   F   E   H   V   R   M   V   D   P   K   K   A   A   Q   I   R   S
GAAAGACAGA CAGCACACCC TAAAGCATTT TGAACATGTG CGCATGGTGG ACCCCAAGAA AGCTGCTCAG ATCCGGTCCC

Q   V   M   T   H   L   R   V   I   Y   E   R   M   N   Q   S   L   L   Y   N   V   P   A   V   A
AGGTTATGAC ACACCTCCGT GTGATCTACG AGCGCATGAA CCAGTCTCTG TCCCTGCTCT ACAATGTCCC TGCGGTGGCT

E   E   I   Q   D   E   V   D   E   L   L   Q   K   B   Q   N   Y   S   D   D   V   L   A   N   M   I   S
GAGGAGATTC AAGATGAAGT CGATGAGCTG CTTCAGAAGG AGCAGAACTA CTCCGACGAT GTCTTGGCCA ACATGATCAG

E   P   R   I   S   Y   G   N   D   A   L   M   P   S   L   T   E   T   K   T   T   V   E   L   L   P
TGAGCCCAGA ATCAGCTACG GAAACGACGC TCTCATGCCT TCGCTGACGG AAACCAAGAC CACCGTGGAG CTCCTTCCCG

V   N   G   E   F   S   L   D   D   L   Q   P   W   H   P   F   G   V   D   S   V   P   A   N   T   E   N
TGAATGGGGA ATTCAGCCTG GATGACCTTC AGCCGTGGCA CCCTTTTGGG GTGGACTCTG TGCCAGCCAA TACCGAAAAT

E   V   E   P   V   D   A   R   P   A   A   D   R   G   L   T   T   R   P   G   S   G   L   T   N   I   K
GAAGTGGAGC CTGTTGACGC CCGCCCCGCT GCTGACCGAG GACTGACCAC TCGACCAGGT TCTGGGCTGA CAAACATCAA

T   E   E   I   S   E   V   K   M   D   A   E   F   G   H   D   S   G   F   E   V   R   H   Q   K   L
GACGGAAGAG ATCTCGGAAG TGAAGATGGA TGCAGAATTC GGACATGATT CAGGATTTGA AGTCCGCCAT CAAAAACTGG

V   F   F   A   E   D   V   G   S   N   K   G   A   I   I   G   L   M   V   G   G   V   V   I   A   T   V
TGTTCTTTGC TGAAGATGTG GGTTCGAACA AAGGCGCCAT CATCGGACTC ATGGTGGGCG GCGTTGTCAT AGCAACCGTG

I   V   I   T   L   V   M   L   K   K   K   Q   Y   T   S   I   H   H   G   V   E   V   D   A   A   V
ATTGTCATCA CCCTGGTGAT GTTGAAGAAG AAACAGTACA CATCCATCCA TCATGGCGTG GTGGAGGTCG ACGCCGCCGT

T   P   E   E   R   H   L   S   K   M   Q   Q   N   G   Y   E   N   P   T   Y   K   F   F   E   Q   M
GACCCCGGAG GAGCGGCCATC TCTCCAAGAT GCAGCAGAAC GGATATGAGA ATCCAACTTA CAAGTTCTTT GAGCAAATGC

Q   N   #
AGAAC TAA
```

```
SAM P8   MLPSLALLLL AAWTVRALEV PTDGNAGLLA EPQIAMFCGK LNMHMNVQNG KWESDPSGTK TCIGTKEGIL
MOUSE    MLPSLALLLL AAWTVRALEV PTDGNAGLLA EPQIAMFCGK LNMHMNVQNG KWESDPSGTK TCIGTKEGIL
RAT      MLPSLALLLL AAWTVRALEV PTDGNAGLLA EPQIAMFCGK LNMHMNVQNG KWESDPSGTK TCIGTKEGIL
MONKEY   MLPGLALLLL AAWTARALEV PTDGNAGLLA EPQIAMFCGR LNMHMNVQNG KWDSDPSGTK TCIDTKEGIL
HUMAN    MLPGLALLLL AAWTARALEV PTDGNAGLLA EPQIAMFCGR LNMHMNVQNG KWDSDPSGTK TCIDTKEGIL

QYCQEVYPEL QITNVVEANQ PVTIQNWCKR GRKQCKTHTH IVIPYRCLVG EFVSDALLVP DKCKFLHQER
         QYCQEVYPEL QITNVVEANQ PVTIQNWCKR GRKQCKTHTH IVIPYRCLVG EFVSDALLVP DKCKFLHQER
         QYCQEVYPEL QITNVVEANQ PVTIQNWCKR GRKQCKTHTH IVIPYRCLVG EFVSDALLVP DKCKFLHQER
         QYCQEVYPEL QITNVVEANQ PVTIQNWCKR GRKQCKTHPH FVIPYRCLVG EFVSDALLVP DKCKFLHQER
         QYCQEVYPEL QITNVVEANQ PVTIQNWCKR GRKQCKTHPH FVIPYRCLVG EFVSDALLVP DKCKFLHQER

MDVCETHLHW HTVAKETCSE KSTNLHDYGM LLPCGIDKFR GVEFVCCPLA EESDSVDSAD AEEDDSDVWW
         MDVCETHLHW HTVAKETCSE KSTNLHDYGM LLPCGIDKFR GVEFVCCPLA EESDSVDSAD AEEDDSDVWW
         MDVCETHLHW HTVAKETCSE KSTNLHDYGM LLPCGIDKFR GVEFVCCPLA EESDSIDSAD AEEDDSDVWW
         MDVCETHLHW HTVAKETCSE KSTNLHDYGM LLPCGIDKFR GVEFVCCPLA EESDNVDSAD AEEDDSDVWW
         MDVCETHLHW HTVAKETCSE KSTNLHDYGM LLPCGIDKFR GVEFVCCPLA EESDNVDSAD AEEDDSDVWW

GGADTDYADG GEDKVVEVAE EEEVADVEEE EADDDEDVED GDEVEEEAEE PYEEATERTT SIATTTTTTT
         VGADTDYADG GEDKVVEVAE EEEVADVEEE EADDDEDVED GDEVEEEAEE PYEEATERTT SIATTTTTTT
         GGADTDYADG GEDKVVEVAE EEEVADVEEE EAEDDEDVED GDEVEEEAEE PYEEATERTT SIATTTTTTT
         GGADTDYADG SEDKVVEVAE EEEVAEVEEE EADDDEDDED GDEVEEEAEE PYEEATERTT SIATTTTTTT
         GGADTDYADG SEDKVVEVAE EEEVAEVEEE EADDDEDDED GDEVEEEAEE PYEEATERTT SIATTTTTTT

ESVEEVVRVP TTAASTPDAA DKYLETPGDE NEHAHFQKAK ERLEAKHRER MSQVMREWEE AERQAKNLPK
         ESVEEVVRVP TTAASTPDAV DKYLETPGDE NEHAHFQKAK ERLEAKHRER MSQVMREWEE AERQAKNLPK
         ESVEEVVRVP TTAASTPDAV DKYLETPGDE NEHAHFQKAK ERLEAKHRER MSQVMREWEE AERQAKNLPK
         ESVEEVVRVP TTAASTPDAV DKYLETPGDE NEHAHFQKAK ERLEAKHRER MSQVMREWEE AERQAKNLPK
         ESVEEVVRVP TTAASTPDAV DKYLETPGDE NEHAHFQKAK ERLEAKHRER MSQVMREWEE AERQAKNLPK

ADKKAVIQHF QEKVESLEQE AANERQQLVE THMARVEAML NDRRRLALEN YITALQAVPP RPHHVFNMLK
         ADKKAVIQHF QEKVESLEQE AANERQQLVE THMARVEAML NDRRRLDLEN YIIALQAVPP RPHHVFNMLK
         ADKKAVIQHF QEKVESLEQE AANERQQLVE THMARVEAML NDRRRLALEN YITALQAVPP RPHHVFNMLK
         ADKKAVIQHF QEKVESLEQE AANERQQLVE THMARVEAML NDRRRLALEN YITALQAVPP RPRHVFNMLK
         ADKKAVIQHF QEKVESLEQE AANERQQLVE THMARVEAML NDRRRLALEN YITALQAVPP RPRHVFNMLK

KYVRAEQKDR QHTLKHFEHV RMVDPKKAAQ IRSQVMTHLR VIYERMNQSL SLLYNVPAVA EEIQDEVDEL
         KYVRAEQKDR QHTLKHFEHV RMVDPKKATQ IRSQVMTHLR VIYERMNQSL SLLYNVPAVA EEIQDEVDEL
         KYVRAEQKDR QHTLKHFEHV RMVDPKKAAQ IRSQVMTHLR VIYERMNQSL SLLYNVPAVA EEIQDEVDEL
         KYVRAEQKDR QHTLKHFEHV RMVDPKKAAQ IRSQVMTHLR VIYERMNQSL SLLYNVPAVA EEIQDEVDEL
         KYVRAEQKDR QHTLKHFEHV RMVDPKKAAQ IRSQVMTHLR VIYERMNQSL SLLYNVPAVA EEIQDEVDEL

LQKEQNYSDD VLANMISEPR ISYGNDALMP SLTETKTTVE LLPVNGEFSL DDLQPWHPFG VDSVPANTEN
         LQKEQNYSDD VLANMISEPR ISYGNDALMP SLTETKTTVE LLPVNGEFSL DDLQPWHPFG VDSVPANTEN
         LQKEQNYSDD VLANMISEPR ISYGNDALMP SLTETKTTVE LLPVNGEFSL DDLQPWHPFG VDSVPANTEN
         LQKEQNYSDD VLANMISEPR ISYGNDALMP SLTETKTTVE LLPVNGEFSL DDLQPWHSFG ADSVPANTEN
         LQKEQNYSDD VLANMISEPR ISYGNDALMP SLTETKTTVE LLPVNGEFSL DDLQPWHSFG ADSVPANTEN
                                                    ↓β                    ↓α
         EVEPVDARPA ADRGLTTRPG SGLTNIKTEE ISEVKMDAEF GHDSGFEVRH QKLVFFAEDV GSNKGAIIGL
         EVEPVDARPA ADRGLTTRPG SGLTNIKTEE ISEVKMDAEF GHDSGFEVRH QKLVFFAEDV GSNKGAIIGL
         EVEPVDARPA ADRGLTTRPG SGLTNIKTEE ISEVKMDAEF GHDSGFEVRH QKLVFFAEDV GSNKGAIIGL
         EVEPVDARPA ADRGLTTRPG SGLTNIKTEE ISEVKMDAEF RHDSGYEVHH QKLVFFAEDV GSNKGAIIGL
         EVEPVDARPA ADRGLTTRPG SGLTNIKTEE ISEVKMDAEF RHDSGYEVHH QKLVFFAEDV GSNKGAIIGL
                   ↓γ
         MVGGVVIATV IVITLVMLKK KQYTSIHHGV VEVDAAVTPE ERHLSKMQQN GYENPTYKFF EQMQN
         MVGGVVIATV IVITLVMLKK KQYTSIHHGV VEVDAAVTPE ERHLSKMQQN GYENPTYKFF EQMQN
         MVGGVVIATV IVITLVMLKK KQYTSIHHGV VEVDAAVTPE ERHLSKMQQN GYENPTYKFF EQMQN
         MVGGVVIATV IVITLVMLKK KQYTSIHHGV VEVDAAVTPE ERHLSKMQQN GYENPTYKFF EQMQN
         MVGGVVIATV IVITLVMLKK KQYTSIHHGV VEVDAAVTPE ERHLSKMQQN GYENPTYKFF EQMQN
```

A
AS  AS  AA  AA  SS  SS  SA  SA  HS  HS  HA  HA
B
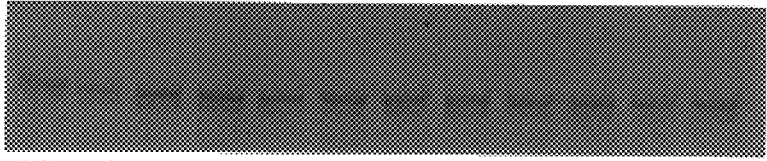
AS  AS  AA  AA  SS  SS  SA  SA  HS  HS  HA  HA
FIGURE 11

SEQUENCE LISTING

<160> NUMBER OF SEQ ID NOS: 20

<210> SEQ ID NO 1
<211> LENGTH: 42
<212> TYPE: DNA
<213> ORGANISM: Homo sapiens
<220> FEATURE:
<223> OTHER INFORMATION: Description of Artificial Sequence: Antisense
      Oligonucleotide

<400> SEQUENCE: 1
ggcgcctttg ttcgaaccca catcttcagc aaagaacacc ag                          42

<210> SEQ ID NO 2
<211> LENGTH: 14
<212> TYPE: DNA
<213> ORGANISM: Homo sapiens
<220> FEATURE:
<223> OTHER INFORMATION: Description of Artificial Sequence: Antisense
      Oligonucleotide

<400> SEQUENCE: 2
aacccacatc ttca                                                         14

<210> SEQ ID NO 3
<211> LENGTH: 2088
<212> TYPE: DNA
<213> ORGANISM: Homo sapiens

<400> SEQUENCE: 3
atgctgccca gcttggcact gctcctgctg gccgcctgga cggttcgggc tctggaggta       60
cccactgatg gcaacgccgg gctgctggca gaaccccaga tcgccatgtt ctgtggtaaa      120
ctcaacatgc acatgaatgt gcagaatgga aagtgggagt cagacccgtc agggaccaaa     180
acctgcattg gcaccaagga gggcatcttg cagtactgcc aagaggtcta ccctgaactg      240
cagatcacaa acgtggtgga agccaaccag ccagtgacca tccagaactg gtgcaagcgg      300
ggccgcaagc agtgcaagac acacacccac atcgtgattc cttaccgttg cctagttggt      360
gagtttgtga gcgacgccct tctcgtgccc gacaagtgca gttcctaca ccaggagcgg       420 atggatgttt gtgagaccca tcttcactgg cacaccgtcg ccaaagagac atgcagcgag      480
aagagcacta acttgcacga ctatggcatg ctgctgccct gcggcatcga caagttccga      540
ggggtagagt ttgtatgctg cccgttggcc gaggaaagcg acagcgtgga ttctgcggat      600
gcagaggagg atgactctga tgtctggtgg ggtggagcgg acacagacta cgctgatggc      660
ggtgaagaca aagtagtaga agtcgccgaa gaggaggaag tggctgatgt tgaggaagag      720
gaagctgatg atgatgagga tgtggaggat gggacgaggt ggaggagga ggccgaggag       780 ccctacgaag aggccaccga gaacaacc agcactgcca ccaccaccac aaccaccact       840
gagtccgtgg aggaggtggt ccgagttccc acgacagcag ccagcacccc cgacgccgcc     900
gacaagtacc tggagacacc cggggacgag aacgagcatg cccatttcca gaaagccaaa      960
gagaggctgg aagccaagca ccgagagaga atgtcccagg tcatgagaga atgggaagag    1020
gcagagcgtc aagccaagaa cttgcccaaa gctgacaaga aggccgttat ccagcatttc    1080
caggagaaag tggaatctct ggaacaggaa gcagccaatg agagacagca gcttgtagag   1140
acacacatgg ccagagttga agccatgctc aatgaccgcc gccgcctggc cctcgagaat    1200
tacatcactg cactgcaggc ggtgcccca aggcctcatc atgtgttcaa catgctgaag    1260

-continued

```
aagtacgtcc gtgcggagca gaaagacaga cagcacaccc taaagcattt tgaacatgtg    1320
cgcatggtgg accccaagaa agctgctcag atccggtccc aggttatgac acacctccgt    1380
gtgatctacg agcgcatgaa ccagtctctg tccctgctct acaatgtccc tgcggtggct    1440
gaggagattc aagatgaagt cgatgagctg cttcagaagg agcagaacta ctccgacgat    1500
gtcttggcca acatgatcag tgagcccaga atcagctacg gaaacgacgc tctcatgcct    1560
tcgctgacgg aaaccaagac caccgtggag ctccttcccg tgaatgggga attcagcctg    1620
gatgacctcc agccgtggca ccctttnggg gtggactctg tgccagccaa taccgaaaat    1680
gaagtcgagc ctgttgacgc ccgccccgct gctgaccgag gactgaccac tcgaccaggt    1740
tctgggctga caaacatcaa gacggaagag atctcggaag tgaagatgga tgcagaattc    1800
ggacatgatt caggatttga agtccgccat caaaaactgg tgttctttgc tgaagatgtg    1860
ggttcgaaca aggcgccat catcggactc atggtgggcg gcgttgtcat agcaaccgtg     1920
attgtcatca ccctggtgat gttgaagaag aaacagtaca catccatcca tcatggcgtg    1980
gtggaggtcg acgccgccgt gaccccagag gagcgccatc tctccaagat gcagcagaac    2040
ggatatgaga atccaactta caagttcttt gagcaaatgc agaactaa                 2088
```

<210> SEQ ID NO 4
<211> LENGTH: 695
<212> TYPE: PRT
<213> ORGANISM: Mouse (SAM P8)

<400> SEQUENCE: 4

```
Met Leu Pro Ser Leu Ala Leu Leu Leu Ala Ala Trp Thr Val Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Ser Val Asp Ser Ala Asp Ala Glu Glu Asp Ser Asp Val
        195                 200                 205

Trp Trp Gly Gly Ala Asp Thr Asp Tyr Ala Asp Gly Gly Glu Asp Lys
    210                 215                 220
```

```
Val Val Glu Val Ala Glu Glu Val Ala Asp Val Glu Glu
225                 230                 235                 240

Glu Ala Asp Asp Glu Asp Val Glu Asp Gly Asp Glu Val Glu Glu
            245                 250                 255

Glu Ala Glu Glu Pro Tyr Glu Ala Thr Glu Arg Thr Thr Ser Thr
                260                 265                 270

Ala Thr Thr Thr Thr Thr Thr Thr Glu Ser Val Glu Val Val Arg
            275                 280                 285

Val Pro Thr Thr Ala Ala Ser Thr Pro Asp Ala Ala Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
                355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro His His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
    530                 535                 540

Pro Trp His Pro Phe Gly Val Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Gly His Asp Ser Gly Phe Glu Val
                595                 600                 605

Arg His Gln Lys Leu Val Phe Phe Ala Glu Asp Val Gly Ser Asn Lys
            610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
```

|   |   |   |   |   |   | 645 |   |   |   | 650 |   |   |   | 655 |   |
|---|---|---|---|---|---|---|---|---|---|---|---|---|---|---|---|

His His Gly Val Val Glu Val Asp Ala Ala Val Thr Pro Glu Glu Arg
                    660                 665             670

His Leu Ser Lys Met Gln Asn Gly Tyr Glu Asn Pro Thr Tyr Lys
            675                 680              685

Phe Phe Glu Gln Met Gln Asn
    690             695

<210> SEQ ID NO 5
<211> LENGTH: 695
<212> TYPE: PRT
<213> ORGANISM: Mouse (Balb C)

<400> SEQUENCE: 5

Met Leu Pro Ser Leu Ala Leu Leu Leu Ala Ala Trp Thr Val Arg
 1               5               10              15

Ala Leu Glu Val Pro Thr Asp Gly Asn Ala Gly Leu Leu Ala Glu Pro
             20              25              30

Gln Ile Ala Met Phe Cys Gly Lys Leu Asn Met His Met Asn Val Gln
         35              40              45

Asn Gly Lys Trp Glu Ser Asp Pro Ser Gly Thr Lys Thr Cys Ile Gly
     50              55              60

Thr Lys Glu Gly Ile Leu Gln Tyr Cys Gln Glu Val Tyr Pro Glu Leu
 65              70              75                          80

Gln Ile Thr Asn Val Val Glu Ala Asn Gln Pro Val Thr Ile Gln Asn
                 85              90              95

Trp Cys Lys Arg Gly Arg Lys Gln Cys Lys Thr His Thr His Ile Val
             100             105             110

Ile Pro Tyr Arg Cys Leu Val Gly Glu Phe Val Ser Asp Ala Leu Leu
         115             120             125

Val Pro Asp Lys Cys Lys Phe Leu His Gln Glu Arg Met Asp Val Cys
     130             135             140

Glu Thr His Leu His Trp His Thr Val Ala Lys Glu Thr Cys Ser Glu
145             150             155                         160

Lys Ser Thr Asn Leu His Asp Tyr Gly Met Leu Leu Pro Cys Gly Ile
                 165             170             175

Asp Lys Phe Arg Gly Val Glu Phe Val Cys Cys Pro Leu Ala Glu Glu
             180             185             190

Ser Asp Ser Val Asp Ser Ala Asp Ala Glu Glu Asp Asp Ser Asp Val
         195             200             205

Trp Trp Val Gly Ala Asp Thr Asp Tyr Ala Asp Gly Gly Glu Asp Lys
     210             215             220

Val Val Glu Val Ala Glu Glu Glu Val Ala Asp Val Glu Glu Glu
225             230             235             240

Glu Ala Asp Asp Asp Glu Asp Val Glu Asp Gly Asp Glu Val Glu Glu
             245             250             255

Glu Ala Glu Glu Pro Tyr Glu Glu Ala Thr Glu Arg Thr Thr Ser Thr
         260             265             270

Ala Thr Thr Thr Thr Thr Thr Thr Glu Ser Val Glu Glu Val Val Arg
     275             280             285

Val Pro Thr Thr Ala Ala Ser Thr Pro Asp Ala Val Asp Lys Tyr Leu
     290             295             300

Glu Thr Pro Gly Asp Glu Asn Glu His Ala His Phe Gln Lys Ala Lys
305             310             315             320

```
Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Leu Val Glu Thr His Met Ala
    370                 375                 380

Arg Val Glu Ala Met Leu Asn Asp Arg Arg Leu Asp Leu Glu Asn
385                 390                 395                 400

Tyr Ile Ile Ala Leu Gln Ala Val Pro Pro Arg Pro His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Thr Gln Ile Arg Ser Gln Val Met Thr His Leu Arg Val Ile Tyr Glu
        450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Pro Phe Gly Val Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Gly His Asp Ser Gly Phe Glu Val
        595                 600                 605

Arg His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 6
<211> LENGTH: 695
<212> TYPE: PRT
<213> ORGANISM: RAT

<400> SEQUENCE: 6
```

-continued

```
Met Leu Pro Ser Leu Ala Leu Leu Leu Ala Ala Trp Thr Val Arg
 1               5                  10                  15

Ala Leu Glu Val Pro Thr Asp Gly Asn Ala Gly Leu Leu Ala Glu Pro
                 20                  25                  30

Gln Ile Ala Met Phe Cys Gly Lys Leu Asn Met His Met Asn Val Gln
             35                  40                  45

Asn Gly Lys Trp Glu Ser Asp Pro Ser Gly Thr Lys Thr Cys Ile Gly
         50                  55                  60

Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Thr His Ile Val
             100                 105                 110

Ile Pro Tyr Arg Cys Leu Val Gly Glu Phe Val Ser Asp Ala Leu Leu
             115                 120                 125

Val Pro Asp Lys Cys Lys Phe Leu His Gln Glu Arg Met Asp Val Cys
         130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                 165                 170                 175

Asp Lys Phe Arg Gly Val Glu Phe Val Cys Cys Pro Leu Ala Glu Glu
             180                 185                 190

Ser Asp Ser Ile Asp Ser Ala Asp Ala Glu Glu Asp Asp Ser Asp Val
             195                 200                 205

Trp Trp Gly Gly Ala Asp Thr Asp Tyr Ala Asp Gly Gly Glu Asp Lys
210                 215                 220

Val Val Glu Val Ala Glu Glu Glu Val Ala Asp Val Glu Glu Glu
225                 230                 235                 240

Glu Ala Glu Asp Asp Glu Asp Val Glu Asp Gly Asp Glu Val Glu Glu
             245                 250                 255

Glu Ala Glu Glu Pro Tyr Glu Glu Ala Thr Glu Arg Thr Thr Ser Ile
             260                 265                 270

Ala Thr Thr Thr Thr Thr Thr Glu Ser Val Glu Glu Val Val Arg
             275                 280                 285

Val Pro Thr Thr Ala Ala Ser Thr Pro Asp Ala Val Asp Lys Tyr Leu
         290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
             325                 330                 335

Glu Trp Glu Glu Ala Glu Arg Gln Ala Lys Asn Leu Pro Lys Ala Asp
             340                 345                 350

Lys Lys Ala Val Ile Gln His Phe Gln Glu Lys Val Glu Ser Leu Glu
             355                 360                 365

Gln Glu Ala Ala Asn Glu Arg Gln Gln Leu Val Glu Thr His Met Ala
         370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro His His Val Phe
             405                 410                 415
```

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
            450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                        485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
            530                 535                 540

Pro Trp His Pro Phe Gly Val Asp Ser Val Pro Ala Asn Thr Glu Asn
545                 550                 555                 560

Glu Val Glu Pro Val Asp Ala Arg Pro Ala Ala Asp Arg Gly Leu Thr
                        565                 570                 575

Thr Arg Pro Gly Ser Gly Leu Thr Asn Ile Lys Thr Glu Glu Ile Ser
                580                 585                 590

Glu Val Lys Met Asp Ala Glu Phe Gly His Asp Ser Gly Phe Glu Val
            595                 600                 605

Arg His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                        645                 650                 655

His His Gly Val Val Glu Val Asp Ala Ala Val Thr Pro Glu Glu Arg
                660                 665                 670

His Leu Ser Lys Met Gln Gln Asn Gly Tyr Glu Asn Pro Thr Tyr Lys
            675                 680                 685

Phe Phe Glu Gln Met Gln Asn
            690                 695

<210> SEQ ID NO 7
<211> LENGTH: 695
<212> TYPE: PRT
<213> ORGANISM: Monkey

<400> SEQUENCE: 7

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                        85                  90                  95

```
Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
    450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
            500                 505                 510
```

-continued

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Lys Met Asp Ala Glu Phe Arg His Asp Ser Gly Tyr Glu Val
        595                 600                 605

His His Gln Lys Leu Val Phe Phe Ala Glu Asp Val Gly Ser Asn Lys
    610                 615                 620

Gly Ala Ile Ile Gly Leu Met Val Gly Val Val Ile Ala Thr Val
625                 630                 635                 640

Ile Val Ile Thr Leu Val Met Leu Lys Lys Lys Gln Tyr Thr Ser Ile
            645                 650                 655

His His Gly Val Val Glu Val Asp Ala Ala Val Thr Pro Glu Glu Arg
        660                 665                 670

His Leu Ser Lys Met Gln Gln Asn Gly Tyr Glu Asn Pro Thr Tyr Lys
    675                 680                 685

Phe Phe Glu Gln Met Gln Asn
    690                 695

<210> SEQ ID NO 8
<211> LENGTH: 695
<212> TYPE: PRT
<213> ORGANISM: Homo sapiens

<400> SEQUENCE: 8

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

-continued

```
Ser Asp Asn Val Asp Ser Ala Asp Ala Glu Asp Asp Ser Asp Val
        195                 200                 205
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Gly Ala Thr Glu Arg Thr Thr Ser Ile
            260                 265                 270
Ala Thr Thr Thr Thr Thr Thr Thr Glu Ser Val Glu Glu Val Val Arg
        275                 280                 285
Val Pro Thr Thr Ala Ala Ser Thr Pro Asp Ala Val Asp Lys Tyr Leu
290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
        355                 360                 365
Gln Glu Ala Ala Asn Glu Arg Gln Gln Leu Val Glu Thr His Met Ala
        370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Arg His Asp Ser Gly Tyr Glu Val
        595                 600                 605
```

```
His His Gln Lys Leu Val Phe Phe Ala Glu Asp Val Gly Ser Asn Lys
            610                 615                 620

Gly Ala Ile Ile Gly Leu Met Val Gly Val Val Ile Ala Thr Val
625                 630                 635                 640

Ile Val Ile Thr Leu Val Met Leu Lys Lys Lys Gln Tyr Thr Ser Ile
                    645                 650                 655

His His Gly Val Val Glu Val Asp Ala Ala Val Thr Pro Glu Glu Arg
                660                 665                 670

His Leu Ser Lys Met Gln Gln Asn Gly Tyr Glu Asn Pro Thr Tyr Lys
            675                 680                 685

Phe Phe Glu Gln Met Gln Asn
    690                 695

<210> SEQ ID NO 9
<211> LENGTH: 14
<212> TYPE: DNA
<213> ORGANISM: Homo sapiens
<220> FEATURE:
<223> OTHER INFORMATION: Description of Artificial Sequence: Antisense
      Oligonucleotide

<400> SEQUENCE: 9
ggcgcctttg ttcg                                                       14

<210> SEQ ID NO 10
<211> LENGTH: 40
<212> TYPE: DNA
<213> ORGANISM: Homo sapiens
<220> FEATURE:
<223> OTHER INFORMATION: Description of Artificial Sequence: Antisense
      Oligonucleotide

<400> SEQUENCE: 10
gatcacgtac acatcgacac cagtcgccat gactgagctt                           40

<210> SEQ ID NO 11
<211> LENGTH: 45
<212> TYPE: DNA
<213> ORGANISM: Homo sapiens
<220> FEATURE:
<223> OTHER INFORMATION: Description of Artificial Sequence: Antisense
      Oligonucleotide

<400> SEQUENCE: 11
tatgacaacg ccgcccacca tgagtccgat gatggcgcct ttgtt                     45

<210> SEQ ID NO 12
<211> LENGTH: 10
<212> TYPE: DNA
<213> ORGANISM: Homo sapiens
<220> FEATURE:
<223> OTHER INFORMATION: Description of Artificial Sequence: Antisense
      Oligonucleotide

<400> SEQUENCE: 12
gatcacgtac                                                            10

<210> SEQ ID NO 13
<211> LENGTH: 14
<212> TYPE: PRT
<213> ORGANISM: Homo sapiens
<220> FEATURE:
<223> OTHER INFORMATION: Description of Artificial Sequence: Amino Acids
      Corresponding to Antisense Oligonucleotide
```

```
<400> SEQUENCE: 13

Leu Val Phe Phe Ala Glu Asp Val Gly Ser Asn Lys Gly Ala
  1               5                  10

<210> SEQ ID NO 14
<211> LENGTH: 4
<212> TYPE: PRT
<213> ORGANISM: Homo sapiens
<220> FEATURE:
<223> OTHER INFORMATION: Description of Artificial Sequence: Amino Acids
      Corresponding to Antisense Oligonucleotide

<400> SEQUENCE: 14

Glu Asp Val Gly
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:  Amino
      Acids Encoded by complement of Antisense Oligonucleotide
      of SEQ ID NO:9

<400> SEQUENCE: 15

Asn Lys Gly Ala
  1

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence:  Amino
      Acids Encoded by complement of Antisense Oligonucleotide
      of SEQ ID NO:11

<400> SEQUENCE: 16

Asn Lys Gly Ala His Gly Leu Met Val Gly Gly Val Val Ile
  1               5                  10

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:  Antisense
      Oligonucleotide

<400> SEQUENCE: 17
gcacacggag cactcggtg                                               19

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:  Antisense
      Oligonucleotide

<400> SEQUENCE: 18
gctgtgaatg tcattta                                                 17

<210> SEQ ID NO 19
<211> LENGTH: 18
<212> TYPE: DNA
```

-continued

```
<213> ORGANISM: Artificial Sequence
<220> FEATURE:
<223> OTHER INFORMATION: Description of Artificial Sequence:  Antisense
      Oligonucleotide

<400> SEQUENCE: 19
atctctgaag tgaagatg                                                        18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:  Antisense
      Oligonucleotide

<400> SEQUENCE: 20
ggtgatgacg atcactgt                                                        18
```

ANTISENSE MODULATION OF AMYLOID BETA PROTEIN EXPRESSION

BACKGROUND OF THE INVENTION (1) Field of the Invention

The present invention relates to compositions and methods for modulating the expression of amyloid beta protein, and more particularly to antisense oligonucleotides that specifically hybridize with nucleic acids encoding human amyloid precursor protein and modulate the expression of the amyloid beta portion of amyloid precursor protein.

(2) Description of the Related Art

Alzheimer's disease is a neurodegenerative disorder characterized by the presence of extracellular senile plaques and intracellular neurofibrillary tangles in the brains of affected individuals. (Masters, C. L. et al., *Proc. Natl. Acad. Sci. USA,* 82:4245–4249 (1985)). The senile plaques, found in abundance in Alzheimer's disease-affected brain cells, are composed of a core of extracellular amyloid beta protein (AβP) surrounded by reactive cells and degenerating neurites. (Lenders, M. B. et al., *Acta Neurologica Belgica,* 89:279–285 (1989); and Perry, G. et al., *Lancet,* 2:746 (1988)). While the plaques form primarily in particular parts of the brain—such as the hippocampus—in some cases they are also found in the walls of cerebral and meningeal blood vessels. (Delacourt, A. et al., *Virchows Archiv.—A, Pathological Analomy & Histopathology,* 411:199–204 (1987); and Masters, C. L. et al., *EMBO Journal,* 4:2757–2763 (1985)).

The major protein subunit of the senile plaques, amyloid beta protein (and also referred to in the art as β-amyloid protein or A4 protein) is a 4 ki) (39–43 amino acid) protein that is a cleavage product of a much larger precursor protein called amyloid precursor protein (APP). Whereas amyloid precursor protein is a transmembrane protein with no known harmful physiological effects, amyloid beta protein is known to be highly aggregating and to deposit and form plaques and to accumulate at high levels in the brain in Alzheimer's disease, Down's syndrome and some normal aged individuals. (Verga, L. et al., *Neuroscience Letters,* 105:294–299 (1989)). Strong evidence that amyloid beta protein deposition plays a critical role in the development of Alzheimer's disease came from the identification of familial Alzheimer's disease kindreds in which the Alzheimer's disease phenotype co-segregates with mutations from the amyloid precursor protein gene. (Younkin, S. G., *Tohuku J. of Exper. Med.,* 174:217–223 (1994); and Matsumura, Y. et al., *Neurology,* 46:1721–1723 (1996)).

Nucleic acid sequences for amyloid precursor protein, amyloid beta protein (AβP), and related proteins have been reported by Ponte et al., (U.S. Pat. No. 5,220,013), and Greenberg et al., (WO88/03951), among others. Amyloid precursor protein has several isoforms generated by alternative splicing of a 19-exon gene made up of exons 1–13, 13a, and 14–18 (Yoshikai et al., *Gene,* 87:257 (1990)). The predominant transcripts are APP695 (exons 1–6, 9–18, not 13a); APP751 (exons 1–7, 9–18, not 13a); and APP770 (exons 1–18, not 13a). All of these encode multidomain proteins with a single membrane spanning region. The AβP segment of amyloid precursor protein comprises approximately one-half of the transmembrane domain and approximately the first 28 amino acids of the extracellular domain of an amyloid precursor protein isoform. (U.S. Pat. No. 5,455,169). This structure is illustrated in FIG. 1, where the 42 amino acid sequence of the AβP segment of mouse amyloid precursor protein is shown—having its C-terminal to the left and an N-terminal portion to the right. That part of the AβP segment that normally resides within the transmembrane domain is enclosed by a dashed oval.

The amyloid precursor protein isoforms differ in that APP751 and APP770, but not APP 695, contain exon 7, which encodes a serine protease inhibitor domain. APP695 is a predominant form in neuronal tissue, whereas APP751 is the predominant variant elsewhere. Beta amyloid protein is derived from that part of the amyloid precursor protein encoded by parts of exons 16 and 17.

Two major pathways of amyloid precursor protein processing in vivo have been described. Normal processing of amyloid precursor protein in the secretory pathway occurs by proteolytic cleavage within the AβP sequence of the amyloid precursor protein resulting in the generation of a large (approximately 100 kD) soluble, secreted N-terminal fragment of the protein (Oltersdorf, T., *Nature,* 14.341, 144–147 (1989); and de Sauvage, F., and J. N. Octave, *Science,* 11:245, 651–653 (1989)) and a smaller (approximately 9–10 kD), membrane-associated C-terminal fragment (Wolf, D. et al., *EMBO Journal,* 9:2079–2084 (1990); and Ghiso, J. et al., *Biochemical Journal,* 288:1053–1059 (1992). FIG. 1 illustrates this type of cleavage as occurring at, or near, the position marked at "α-secretase". Neither of the two protein fragments that result from the cleavage is amyloidogenic (i.e., tends to form senile plaques), because neither of them contains the entire AβP protein.

However, another pathway of amyloid precursor protein metabolism involves the endosomal-lysosomal system and results in generation of an amyloidogenic C-terminal fragment of amyloid precursor protein. When amyloid precursor protein is processed by the endosomal-lysosomal system, a complex set of —COOH terminal derivatives of amyloid precursor protein is produced that includes potentially amyloidogenic forms having the entire AβP at, or near, their N-terminal. One form of this aberrant cleavage of amyloid precursor protein occurs at, or near, the positions identified in FIG. 1 as "β and γ secretases" (Glenner and Wong, Biochem. *Biophys. Res. Commun.,* 122:1131–1135 (1984); Volloch, *FEBS Letters,* 390:124–128 (1996)) and results in the generation of AβP that is known to deposit and form plaques. The plaques have been shown to be associated with the clinical severity of Alzheimer's disease. Abundant deposition of AβP in the brains of patients with Alzheimer's disease has suggested that regulation of amyloid precursor protein expression and metabolism are key pathological events. It is known that some amount of AβP is constantly produced in the brain, but is continuously cleared. Apparently, the two alternative pathways of amyloid precursor protein metabolism must be precisely balanced in order to avoid the accumulation of AβP in harmful concentrations.

It is known that the amyloid precursor protein gene in humans is located on chromosome 21. Several different studies have suggested the apparent involvement of several particular sites in the amyloid precursor protein gene in Alzheimer's disease. Three separate mutations in codon 717 of the amyloid precursor protein transcript have been found in familial Alzheimer's disease: val717-to-ile, val717-to-phe, and val717-to-gly. See, Hardy et al., U.S. Pat. No. 5,877,015. The location of these mutations and of the double mutation disclosed by Mullan (U.S. Pat. No. 5,455,169) suggested to Suzuki et al., *Science,* 264:1336–1340 (1994), that they may cause Alzheimer's disease by altering amyloid beta protein processing in a way that is amyloidogenic. They found that the APP717 mutations were consistently associated with a 1.5- to 1.9-fold increase in the percentage of longer peptide fragments generated and that the longer peptide fragments formed insoluble amyloid fibrils more rapidly than did the shorter ones. Alternative splicing of transcripts from the single amyloid precursor protein gene results in at least 10 isoforms of the gene product (Sandbrink et al., *J. Biol. Chem.,* 269: 1510–1517 (1994)), of which APP695 is preferentially expressed in neuronal tissues. In 3 mutations, valine-642 in the transmembrane domain of APP695 is replaced by isoleucine, phenylalanine, or glycine, in association with dominantly inherited familial Alzheimer's disease. According to an earlier numbering system, val642 was numbered 717 and the 3 mutations were V717I, V717F, and V717G, respectively). Yamatsuji et al., *Embo J.* 15: 498–509 (1996), stated that these 3 mutations account for most, if not all, of the chromosome 21-linked Alzheimer's disease. In transgenic mice, overexpression of such mutants mimics the neuropathology of Alzheimer's disease. Yamatsuji et al., *Science,* 272: 1349–1352 (1996), demonstrated that expression of any 1 of these 3 mutant proteins, but not of normal APP695, induced nucleosomal DNA fragmentation in cultured neuronal cells. Induction of DNA fragmentation required the cytoplasmic domain of the mutants and appeared to be mediated by heterotrimeric guanosine triphosphate-binding proteins (G-proteins).

The use of complimentary sequences to arrest translation of mRNAs was described in the late 1970's (See, e.g., Paterson et al., *Proc. Natl. Acad. Sci.,* 74:4370–4374 (1977); Hastie, N. D. and W. A. Held, *Proc Natl. Acad. Sci.,* 75: 1217–1221 (1978); and Zamecnik, P. C. and M. L. Stephenson, *Proc. Natl. Acad. Sci.,* 75:280–284 (1978)). However, the use of antisense oligonucleotides for selective blockage of specific mRNAs is of recent origin. (See, e.g., Weintraub et al, *Trends Gen.,* 1:22–25 (1985); Loke et al., *Prod. Natl. Acad. Sci, USA,* 86:3474–3478 (1989); Mulligan et al., *J. Med. Chem.,* 36:1923–1937 (1993); and Wagner, *Nature,* 372:333–335 (1994)). The mechanism of antisense inhibition in cells was previously analyzed and the decrease in mRNA levels mediated by oligonucleotides was shown to be responsible for the decreased expression of several proteins. (See, Walder, R. Y. and J. A. Walder, *Proc. Natl. Acad. Sci. USA,* 85:5011–5015 (1988); Dolnick, B. J., *Cancer Invest.,* 9:185–194 (199 1); Crooke S. and B. LeBleu, *Antisense Research and Applications,* CRC Press, Inc., Boca Raton, Fla. (1993); Chiang et al., *J. Biol. Chem.,* 266:18162–18171 (1991); and Bennett et al., *J. Immunol.,* 152:3530–3540 (1994)).

The use of antisense oligonucleotides is recognized as a viable option for the treatment of diseases in animals and man. For example, see U.S. Pat. Nos. 5,098,890, 5,135,917, 5,087,617, 5,166,617, 5,166,195, 5,004,810, 5,194,428, 4,806,463, 5,286,717, 5,276,019, 5,264,423, 4,689,320, 4,999,421 and 5,242,906, which teach the use of antisense oligonucleotides in a variety of diseases including cancer, HIV, herpes simplex virus, influenzavirus, HTLV-HI replication, prevention of replication of foreign nucleic acids in cells, antiviral agents specific to CMV, and treatment of latent EBV infections.

Recently, it has been recognized that regulation of the expression of the amyloid precursor protein gene could be useful for the detection and treatment of diseases associated with deposition of APP. For example, Salbaum et al. (U.S. Pat. No. 5,853,985) reported the use of the promoter for human amyloid precursor protein in a method for screening for a drug that regulates the expression of the amyloid precursor protein gene. Monia et al., (U.S. Pat. No. 5,837, 449) described oligonucleotide probes that could selectively hybridize to an amyloid precursor protein gene having mutations at codons 717, 670 and 671 of the APP770 isoform, and serve for detection as well as for modulation of the expression of AβP. Besides the mutations at codons 717, 670 and 671 of APP770, Monia et al. suggested that the same mutations at codons 642, 595 and 596 of the shorter isoform—APP695—may be expected to provide similar effects. Nevertheless, the use of such oligonucleotides has not yet been proven to be an effective treatment for diseases involving the expression of amyloid beta protein.

Thus, despite significant advances in the understanding of the pathology of Alzheimer's disease and related diseases, there still is a need for methods to regulate the expression of amyloid beta protein; especially a method that could improve the acquisition and retention capabilities of animals that were affected by, or at risk of being affected by diseases that were related to the deposition of AβP in the brain.

SUMMARY OF THE INVENTION

Briefly, therefore, the inventor has succeeded in discovering that novel antisense compounds comprising nucleotides complementary to a nucleic acid sequence coding for amyloid precursor protein inhibit the expression of an amyloid beta protein portion of the amyloid precursor protein coding sequence while permitting the expression of at least a portion of the amyloid precursor protein polynucleotide 5' to the AβP portion of the amyloid precursor protein coding sequence.

Thus, in one embodiment, the present invention is directed to novel oligonucleotides, in particular the sequence GGCGCCTTTGTTCGAACCCACATCT- TCAGCAAAGAACACCAG (SEQ ID NO: 1), which is complementary to nucleotides that encode for amino acids 17–30 (SEQ ID NO:13) of the amyloid beta protein portion of amyloid precursor protein, and the sequence AACCCA- CATCTTCA (SEQ ID NO:2), which is complementary to nucleotides that encode for amino acids 22–25 (Glu Asp Val Gly—SEQ ID NO: 14) of the amyloid beta protein portion of amyloid precursor protein.

The present invention, in another embodiment, is directed to a novel method for modulating the expression of amyloid beta protein in cells or tissues comprising contacting said cells or tissues with one or more of the antisense compounds that bind to the polynucleotide encoding amyloid beta protein, in particular, SEQ ID NO:1 and SEQ ID NO:2.

In another embodiment, the present invention is directed to a novel method for treating or preventing a disease or condition associated with the expression of amyloid beta protein in a vertebrate, including a mammal, and, in particular, a human, the method comprising administering to the vertebrate, mammal, or human an AβP inhibitory effective amount of one or more of the antisense compounds that bind to the polynucleotide encoding amyloid beta protein, in particular, SEQ ID NO:1 and SEQ ID NO:2.

The present invention is also directed to a novel recombinant DNA or RNA molecule having a DNA or RNA sequence which, on transcription, produces an antisense RNA against amyloid beta protein or its complement, said antisense RNA comprising a nucleic acid segment which specifically hybridizes to the polynucleotide encoding amyloid precursor protein, in particular, one of the nucleic acid molecules of SEQ ID NOS:1 or 2.

The present invention is also directed to a novel method to improve cognitive abilities in a mammal having a disease or condition that is associated with the expression of amyloid beta protein, the method comprising administering to the mammal an AβP inhibitory effective amount of at least one of the antisense compounds comprising nucleotides complementary to a nucleic acid sequence coding for amyloid precursor protein inhibit the expression of an amyloid beta protein portion of the amyloid precursor protein coding sequence while permitting the expression of at least a portion of the amyloid precursor protein polynucleotide 5' to the AβP portion of the amyloid precursor protein coding sequence.

Among the several advantages found to be achieved by the present invention, therefore, may be noted the provision of compounds and methods which are useful for the regulation of the expression of AβP; the provision of compounds and methods that improve the retention and acquisition capabilities in animals that have been affected by diseases that are related to the deposition of AβP in the brain; and the provision of compounds and methods which are useful in preventing the development of diseases causing deposition of amyloid beta protein in the brain.

BRIEF DESCRIPTION OF THE DRAWINGS

FIG. 3 shows the nucleotide sequence (SEQ ID NO:3) and corresponding amino acid sequence (SEQ ID NO:4) of amyloid precursor protein (APP695 amino acid isoform) cloned from SAM P8 mouse hippocampus with initiation and termination codons enclosed in boxes; with the portion of the sequence coding for amyloid beta protein being underlined; and with the portion that is complementary to SEQ ID NO:1 (OL-1) having a double underline;

FIG. 4 shows a comparison of the aligned amino acid sequences of amyloid precursor protein from SAM-P8 mice, Balb C mice, rat, monkey, and human with nucleotide differences marked by bolded letters, and showing the site of action of beta, alpha and gamma secretases marked by arrows (SEQ ID NO: 4–8, respectively);

FIGS. 11(A–B), track "A", is a Western blot showing the relative concentration of the C-terminal portion of amyloid precursor protein in tissue samples recovered from three groups of four SAM P8 mice; in the three groups, tissue samples were removed from the amygdala (A), hippocampus (H), or septum (S) regions of four mice—two of which received administration of a saline vehicle (S), and the other two of which had received administration of antisense oligonucleotide OL-1 (SEQ ID NO:1) (A) and indicating the presence of amyloid precursor protein in all samples from mice receiving saline, but significant inhibition of the expression of the C-terminal portion of amyloid precursor protein in mice receiving the antisense oligonucleotide; track "B" is a Northern blot showing the APP mRNA content of the same tissue samples as developed by an RNase protection assay and indicating no effect on mRNA levels by either of the two treatments; in both track "A" and track "B" the first letter of a sample describes the location of the source of the tissue sample and the second letter describes whether the mouse received saline or an antisense oligonucleotide.

DETAILED DESCRIPTION OF THE PREFERRED EMBODIMENTS

Figure 1:
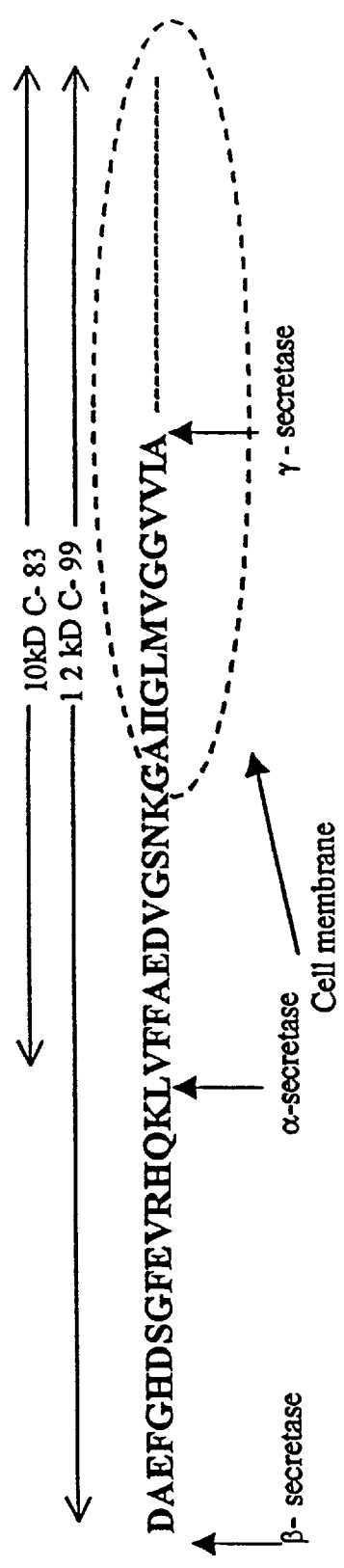
FIG. 1 depicts a portion of a mouse amyloid precursor protein molecule with the amino acid sequence of the AβP segment elucidated (showing AβP amino acids 1 through 42)(residues 1–42 of SEQ ID NO:3); and indicating the locations of protease action by α, β, and γ-secretases (with the C-terminal fragments resulting from cleavage by, respectively, α and β secretases indicated by the lines above the sequence); and showing the location of the transmembrane section of the protein as enclosed by a dashed oval.

In accordance with the present invention, it has been discovered that oligonucleotides, which are complementary to certain locations within a nucleic acid sequence encoding amyloid precursor protein, modulate—and, in particular, inhibit—the expression of the AβP portion of amyloid precursor protein. Among the antisense oligonucleotides that demonstrate such activity, a 42 contiguous nucleotide-base oligonucleotide labeled OL-1 (SEQ ID NO: 1) and a 14 contiguous nucleotide-base oligonucleotide labeled OL-3 (SEQ ID NO:2) are preferred due to their effectiveness as nhibitors of AβP synthesis. Both of the oligonucleotides complement some or all of the nucleic acids coding for AβP amino acids numbered 17–30, in the AβP coding region of APP mRNA. These oligonucleotides inhibit the synthesis of the AβP portion of amyloid precursor protein—and, in particular, that portion of APP that includes AβP amino acids 22 to 25—while permitting the expression of at least a portion of the amyloid precursor protein polypeptide that is 5' to the AβP portion of the amyloid precursor protein coding sequence. The subject oligonucleotides regulate the expression of AβP in vitro in mammalian cells and in vivo in senescence accelerated mice (SAM-P8) mice. Surprisingly, these oligonucleotides cause the reversal of the age-related acquisition and retention deficits that are normally observed in the SAM-P8 mice.

Regulation of mRNA to control the expression of a specific protein is performed by different molecular techniques. One technique that functions in a variety of systems is antisense oligonucleotide technology. (Wagner, *Nature*, 372:333–335 (1994); Wagner et al., *Science*, 26:1510–1513 (1995); Smith et al., *Nature*, 334:724–726 (1988); and Symons, *Trends in Biochem. Sci.*, 14:445–452 (1989)). However, merely knowing complementary sequences for a particular mRNA does not provide a method for selecting antisense oligonucleotides that will have the desired regulatory effects at a useful potency. (See, e.g., Wagner, (1994) id at 334). Moreover, the physiological effects of the administration of antisense oligonucleotides to cells and/or animals cannot be predicted a priori. For example, Tanzi et al., in U.S. Pat. No. 5,643,726, discloses amyloid precursor-like proteins that down-regulated the expression from the amyloid precursor protein promoter. However, the inventor has learned that blockage of the expression of all amyloid precursor protein may create undesirable health effects, since total inhibition of the expression of amyloid precursor protein in mice causes the mice to become very sick (Kumar et al., unpublished data). But the inventor has been found that the subject oligonucleotides have the surprising capability of providing for the regulation of AβP without also inhibiting the formation of at least some—or some part of—amyloid precursor protein. Thus, the subject antisense oligonucleotides result in AβP regulation, while avoiding undesirable consequences of inhibiting the synthesis of the total amyloid precursor protein molecule.

The present invention employs oligonucleotides that specifically hybridize to nucleic acids that encode AβP. In particular, the subject oligonucleotides specifically hybridize to nucleic acids coding for AβP amino acids 17–30, or to at least 12; more preferably to at least 14; even more preferably to at least 18; yet more preferably to at least 22; and even more preferably to about 42 nucleic acids within the polynucleotide coding for amyloid beta protein amino acids numbered 17–30 of the region of amyloid precursor protein that encodes AβP. Furthermore, this region of the amyloid beta protein polypeptide is essential for the antisense composition and method of the present invention, because oligonucleotides that hybridize to nucleic acids that are downstream from this site—in particular, downstream from AβP amino acid 27—or to nucleic acids that lie upstream from this site, but outside of the AβP coding region, had no effect on the reversal of memory deficits in mice. It is preferred that the antisense compound hybridize to nucleic acids that are contiguous.

An oligonucleotide that contains complementary nucleic acids to a target nucleic acid is commonly referred to as an "antisense" oligonucleotide. "Targeting" an oligonucleotide to a chosen nucleic acid, so that the oligonucleotide specifically hybridizes to the target, is a multistep process that begins with identifying a nucleic acid sequence whose function is to be modulated. In the present invention, the antisense nucleic acid sequence is complementary to the AβP encoding region specified by means of the amyloid precursor protein gene, or the mRNA encoded by the amyloid precursor protein gene. The targeting process also includes determination of a site or sites within the nucleic acid sequence for the oligonucleotide interaction to occur such that the desired effect, namely, modulation of expression of the AβP gene, will result. Once the target site or sites have been identified, oligonucleotides are chosen which are sufficiently complementary to the target, i.e., bind sufficiently well and with sufficient specificity, to give the desired modulation.

As used herein, the terms "modulation" and "regulation" are meant to include either inhibition or stimulation of gene expression. In the context of the present invention, inhibition of AβP expression is the type of modulation that is desired. This modulation can be measured by methods that are known in the art and which are described in the examples that follow. Such methods have been described, among others, by Sambrook et al., *Molecular Cloning: A Laboratory Manual*, Cold Spring Harbor Laboratory Press, NY (1989). For example, RNA expression can be measured by Northern blot or slot blot hybridization assays, primer extension and poly A+ assays. Western blot assays, radioimmunoassays and enzyme-linked immunoabsorbent assays can be used to measure protein.

As used herein to describe the regulatory effect that a compound has on the expression of a gene, the term "inhibition" means that the compound reduces the expression of the gene to some degree compared with its expression under the same conditions, but without the presence of the compound. Inhibitory compounds commonly demonstrate concentration dependant activity, wherein increased concentrations of such compounds demonstrate higher levels of inhibition. When the terms "inhibitory effective amount" are used herein with respect to an inhibitory compound, what is meant is an amount of an antisense compound that inhibits the expression of a gene to a measurable degree. Such inhibitory effective amount preferably reduces the level of expression by at least about 25%; more preferably, by at least about 50%; even more preferably by at least about 75%; and most preferably by at least about 80%, or more. Thus, an "AβP inhibitory effective amount" of an antisense compound refers to an amount of the antisense compound that has the level of inhibitory effect upon the expression of AβP that is described above.

The term "hybridization", as used herein, means hydrogen bonding, which may be Watson-Crick, Hoogsteen or reversed Hoogsteen hydrogen bonding, between complementary nucleotide bases. For example, adenine and thiamine, and guanine and cytosine, respectively, are complementary nucleobases that pair through the formation of hydrogen bonds. "Complementary", as that term is used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are complementary to each other at that position. The oligonucleotide and the DNA or RNA are complementary to each other when a sufficient number of corresponding positions in each molecule are occupied by nucleotides that can hydrogen bond with each other. "Specifically hybridize" means that a particular sequence has a sufficient degree of complementarity or precise pairing with a DNA or RNA target sequence that stable and specific binding occurs between the oligonucleotide and the DNA or RNA target. It is understood in the art that the sequence of an antisense compound need not be 100% complementary to that of its target nucleic acid to be specifically hybridizable. Typically, for specific hybridization in vitro, moderate stringency conditions are used such that hybridization occurs between substantially similar nucleic acids, but not between dissimilar nucleic acids. In in vitro systems, stringency conditions are dependent upon time, temperature and salt concentration as can be readily determined by the skilled artisan. (See, e.g., Sambrook et al., *Molecular Cloning: A Laboratory Manual*, Cold Spring Harbor Laboratory Press, NY (1989)). For in vivo antisense methods, the hybridization conditions consist of intracellular conditions which govern the hybridization of the antisense oligonucleotide with the target sequence. An antisense compound specifically hybridizes to the target sequence when binding of the compound to the target DNA or RNA molecule interferes with the normal translation of the target DNA or RNA such that a functional gene product is not produced, and there is a sufficient degree of complementarity to avoid non- specific binding.

As used herein, the term "antisense compound" is meant to include, but not be limited to, antisense oligonucleotides, and is intended to include other chemical compounds that specifically bind to the same targeted nucleic acids that are described below, and that provide the same regulatory effect on AβP expression as the subject antisense oligonucleotides. The antisense oligonucleotides of the present invention are synthesized in vitro and do not include antisense oligonucleotides of biological origin, except for oligonucleotides that comprise the subject antisense oligonucleotides and which have been purified from or isolated from such biological material.

The antisense compounds in accordance with this invention preferably comprise from about 12 to about 42 nucleotides; and more preferably comprise from about 14 to about 42 nucleotides. However, an antisense compound of even fewer than 12 nucleotides—for example, a fragment of the preferred antisense compound—is understood to be included within the present invention so long as it demonstrates the desired activity of inhibiting the expression of an amyloid beta protein portion of the amyloid precursor protein coding sequence while permitting the expression of at least a portion of the amyloid precursor protein polynucleotide 5' to the amyloid beta portion of the amyloid precursor protein coding sequence. It is preferred that the nucleotides of the present antisense compound be contiguous. The subject antisense oligonucleotides are oligonucleotides that are targeted to the portion of the amyloid precursor protein nucleic acid that encodes amino acids numbered from 613 to 626 of APP695 (SEQ ID NO: 13). It is believed that the subject antisense oligonucleotides modulate the expression of amyloid precursor protein genes encoding all isoforms of amyloid precursor protein, including APP563, APP714, APP751 and APP770 isoforms of amyloid precursor protein.

Preferred antisense oligonucleotides of the present invention are: GGCGCCTTTGTTCGAACCCACATCT-TCAGCAAAGAACACCAG; (SEQ ID NO: 1); or AAC-CCACATCTTCA; (SEQ ID NO:2).

The antisense nucleotide SEQ ID NO:1 is targeted to nucleic acids that code for amino acids numbered 17–30 of the AβP portion of amyloid precursor protein (i.e., amino acids numbered 613 to 626 of APP695), namely, LVFFAED-VGSNKGA (SEQ ID NO: 13); and antisense oligonucleotide SEQ ID NO:2 is targeted to nucleic acids that code for amino acids numbered 22–25 of the AβP portion of amyloid precursor protein (i.e., amino acids numbered 618 to 621 of APP695), namely, EDVG (SEQ ID NO: 14).

The most preferred antisense oligonucleotide is SEQ ID NO:1.

It is an advantageous property of the subject antisense compounds that, while they inhibit the expression of amyloidogenic AβP, or at least that portion of AβP that is required for it to be amyloidogenic, they permit the expression of at least a portion of the amyloid precursor protein nucleotide that is 5' to the APP portion of the coding sequence. It is preferred that such portion of the amyloid precursor protein nucleotide 5' to the AβP portion of the coding sequence is one that is at least about 20 nucleotides in length; more preferably about 200 nucleotides in length; and most preferably comprises the entire portion of the amyloid precursor protein coding sequence 5' to the AβP portion of the amyloid precursor protein coding sequence. One isoform of the amyloid precursor protein coding sequence is shown as SEQ ID NO:3.

While antisense oligonucleotides are a preferred form of antisense compound, the present invention contemplates other oligomeric antisense compounds, including, but not limited to, oligonucleotide mimetics those containing modified backbones (which may be referred to herein as "modified internucleoside linkages). As defined herein, oligonucleotides having modified backbones include those that retain a phosphorous atom in the backbone, as well as those that do not have a phosphorous atom in the backbone.

Modified oligonucleotide backbones which are useful in the subject antisense oligonucleotides include, for example, phosphorothioates, chiral phosphorothioates, phosphorodithioates, phosphotriesters, aminoalkylkphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, and boranophosphonates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. References that teach the preparation of such modified backbone oligonucleotides are provided, for example, in U.S. Pat. No. 5,945,290.

Modified oligonucleotide backbones that do not include a phosphorous atom therein may comprise short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; alkene-containing backbones; sulfamate backbones; methylene-imino and methylenehydrazino backbones; sulfonate and sulfonamide backbones; amide backbones; and others having mixed N, O, S and $CH_2$ component parts. References that teach the preparation of the oligonucleotides listed above are provided in U.S. Pat. No. 5,945,290.

Other useful oligonucleotide mimetics, which are useful in the subject antisense oligonucleotides, comprise replacement of both the sugar and the internucleoside linkage—i.e., the backbone—of the nucleotide units with novel groups. One such oligomeric compound that has excellent hybridization properties is a peptide nucleic acid. See, e.g., Nielsen et al., *Science*, 254:1497–1500 (1991); and U.S. Pat. Nos. 5,539,082; 5,714,331; and 5,719,262. In such peptide nucleic acid compounds the sugar-backbone of an oligonucleotide is replaced with an amide containing backbone, in particular with an aminoethylglycine backbone. The nucleobases are retained and are bound directly or indirectly to aza nitrogen atoms of the amide portion of the backbone.

Other useful modified oligonucleotides are those having phosphorothioate backbones and oligonucleotides with heteroatom backbones, and in particular —$CH_2$—NH—O—$CH_2$—, —$CH_2$—N($CH_3$)—O—$CH_2$—, —$CH_2$—O—N($CH_3$)—$CH_2$—. —$CH_2$—N($CH_3$)—N($CH_3$)—$CH_2$—, and —O—N($CH_3$)—$CH_2$—$CH_2$—, wherein the native phosphodiester backbone is represented as —O—P—O—$CH_2$—, (as disclosed in U.S. Pat. No. 5,489,677), and the amide backbones disclosed in U.S. Pat. No. 5,602,240. Also useful are oligonucleotides having morpholino backbone structures as taught in U.S. Pat. No. 5,304,506.

Modified oligonucleotides can also contain one or more substituted sugar moieties (which may be referred to herein as "modified sugar moieties"). Useful oligonucleotides comprise one of the following at the 2' position: OH; F; O—, S—, N-alkyl; N-alkenyl; N-alkynyl; or O-alkyl-O-alkyl, wherein the alkyl, alkenyl, or alkynyl may be substituted or unsubstituted $C_1$ to $C_{10}$ alkyl, or $C_2$ to $C_{10}$ alkenyl and alkynyl; O($CH_2$)O($CH_3$); O($CH_2$)O($CH_2$)$_n$$CH_3$; O($CH_2$)$_n$$NH_2$; or O($CH_2$)$_n$$CH_3$ (where n=1 to 10); Cl; Br; CNB; $CF_3$; $OCF_3$; $NO_2$; $N_3$; $NH_2$; heterocycloalkyl; heterocycloalkaryl; aminoalkylamino; polyalkylamino; substituted silyl; an RNA cleaving group; a cholesterol group; a reporter group; an intercalator; a group for improving the pharmacokinetic properties of an oligonucleotide; or a group for improving other substituents having similar properties. Oligonucleotides can also have sugar mimetics such as cyclobutyls in place of the pentafuranosyl group. A preferred modified sugar moiety is a 2'-O-methoxyethyl sugar moiety.

Other useful antisense compounds may include at least one nucleobase modification or substitution. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine, 5-hydroxymethylcytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocystine, 5-halouracil and cytosine, 5-propynyl uracil and cytosine, 6-azo uracil, cytosine and thymine, 5-uracil, 4-thiouracil, 8-halo, 8-amino, 8-thiol, 8-thioalkyl, 8-hydroxyl and other 8-substituted adenines and guanines, 5-halo, particularly 5-bromo, 5-trifluromethyl and other 5-substitutes uracils and cytosines, 7-methylguanine and 7-methyladenine, 8-azaguanine and 8-azaadenine, 7-deazaguanine and 7-deazaadenine and 3-deazaguanine and 3-deazaadenine.

The antisense compounds of the present invention may be conveniently and routinely made through the well-known technique of solid phase synthesis. Equipment for such synthesis is available from several manufacturers and vendors including, for example, Applied Biosystems, Foster City, Calif. Any other means for such synthesis known in the art may additionally or alternatively be employed. It is also well known to use similar techniques to prepare modified oligonucleotides such as the phosphorothionates and alkylated derivatives that are discussed above.

The subject antisense compounds can be used in a method to modulate the expression of AβP in cells or tissues. In the method, one or more of the antisense compounds, is contacted with the cells or tissues. In a preferred embodiment, the antisense compound(s) is administered in an AβP inhibitory effective amount. The effect of the antisense compound (s) is to inhibit the expression of APP by the cells or tissues.

For therapeutics, methods of treating a condition arising from abnormal AβP expression and/or clearing are provided. As used herein, the terms "abnormal AβP expression" refer to overproduction of AβP, or production of mutant AβP including, but not limited to, mutant forms of AβP with mutations at codons 717, 670 and/or 671 (of APP770). The formulation of therapeutic compositions and their subsequent administration is believed to be within the skill of those in the art. In general, for therapeutics, a patient suspected of having, or being prone to a disease or condition associated with the expression of AβP can be treated by administering to the patient one or more of the subject antisense oligonucleotides, commonly in a pharmaceutically acceptable carrier, in amounts and for periods of time which will vary depending upon the nature of the particular disease, its severity and the patient's overall condition. In general, it is preferred that the antisense compound is administered to the patient in an AβP inhibitory effective amount. In one embodiment of the present invention, the disease is Alzheimer's disease.

In one preferred embodiment of the present invention, the patient is a vertebrate; more preferably a mammal; and most preferably a human.

A "pharmaceutically acceptable carrier" (also referred to herein as an "excipient") is a pharmaceutically acceptable solvent, suspending agent or any other pharmacologically inert vehicle for delivering one or more of the subject antisense oligonucleotides to an vertebrate. The pharmaceutically acceptable carrier may be a liquid or a solid and is selected with the planned manner of administration in mind so as to provide for the desired bulk, consistency, and other pertinent transport and chemical properties, when combined with one or more of the subject antisense oligonucleotides and any other components of a given pharmaceutical composition. Typical pharmaceutically acceptable carriers include, but are not limited to, saline solution; binding agents (e.g., pregelatinized corn starch, polyvinylpyrrolidone or hydroxypropyl methylcellulose, or etc.); fillers (e.g., lactose and other sugars, microcrystalline cellulose, pectin, gelatin, calcium sulfate, ethyl cellulose, polyacrylates or calcium hydrogen phosphate, and the like); lubricants (e.g., magnesium stearate, starch, polyethylene glycol, sodium benzoate, sodium acetate, and the like); disintegrates (e.g., starch, sodium starch glycolate, and the like); or wetting agents (e.g., sodium lauryl sulfate, and the like).

The pharmaceutical compositions of this invention may be administered in a number of ways depending upon whether local or systemic treatment is desired, and upon the area to be treated. Administration may be topical (including opthalmic, vaginal, rectal, intranasal, transdermal), oral or parenteral, for example, by intravenous drip, subcutaneous, intraperitoneal or intramuscular injection or intrathecal or intraventricular administration, such as, for example, by intracerebral ventricular injection (ICV). It is believed that the subject antisense oligonucleotides can also be administered by tablet, since the toxicity of the oligonucleotides is very low. Administration can be either rapid as by injection or over a period of time as by slow infusion or administration of slow release formulations. For treating tissues in the central nervous system, administration can be by injection or infusion into the cerebrospinal fluid. When it is intended that the antisense oligonucleotide of the present invention be administered to cells in the central nervous system, administration can be with one or more agents capable of promoting penetration of the subject antisense oligonucleotide across the blood-brain barrier.

The subject antisense oligonucleotides can also be linked or conjugated with agents that provide desirable pharmaceutical or pharmacodynamic properties. For example, the antisense oligonucleotide can be coupled to any substance known in the art to promote penetration or transport across the blood-brain barrier such as an antibody to the transferrin receptor, and administered by intravenous injection. The antisense compound can be linked with a viral vector, for example, which can make the antisense compound more effective and/or increase the transport of the antisense compound across the blood-brain barrier.

The subject antisense compounds may be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, MD).

The antisense compounds of the present invention can include pharmaceutically acceptable salts, esters, or salts of such esters, or any other compound which, upon administration to an animal, including a human, is capable of providing—directly or indirectly—the biologically active metabolite or residue thereof. Accordingly, for example, the invention is also meant to include prodrugs and pharmaceutically acceptable salts of the compounds of the invention, pharmaceutically acceptable salts of such prodrugs, and other bioequivalents.

As used herein, the term "prodrug" means a therapeutic agent that is prepared in an inactive form that is converted to an active form within the body or cells thereof by the action of endogenous enzymes or other chemicals and/or conditions. The term "pharmaceutically acceptable salts" means physiologically and pharmaceutically acceptable salts of the compounds of the invention: i.e., salts that retain the desired biological activity of the parent compound and do not impart undesired toxicological effects thereto.

The present invention also includes pharmaceutical compositions and formulations that include the antisense compounds of the invention. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for intrathecal or intraventricular administrations may include sterile aqueous solutions which may also contain buffers, diluents and other suitable additives.

Compositions for oral administration include powders or granules, suspensions or solutions in water or non-aqueous media, capsules, sachets or tablets. Thickeners, flavorings, diluents, emulsifiers, dispensing aids or binders may be desirable.

Formulations for parenteral administration may include sterile aqueous solutions which may also contain buffers, diluents and other suitable additives.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

This example illustrates the cloning of the amyloid precursor protein DNA from SAM-P8 mice.

The polynucleotide sequence encoding the 80 kD (695 amino acid) amyloid precursor protein isoform from SAM-P8 mouse brain was cloned by RTPCR technique. The first strand complementary DNA was synthesized using 1 μg of total RNA from the hippocampus of the P8 mouse. The reaction was performed in a total volume of 20 μl, consisting of 10 mM Tris HCl, pH 8.2, 5 mM $MgCl_2$, 0.1 mM DTT, 5 units of RNase inhibitor, 1 μM oligo dT, and 5 units of reverse transcriptase. The mix was incubated at 42° C. for 1 hr and reverse transcriptase was inactivated at 95° C. for 5 min. The reaction mixture was subjected to PCR using forward (5'GCACACGGAGCACTCGGTG) (SEQ ID NO: 17) and reverse primers (5'GCTGTGAATGTCATTTA) (SEQ ID NO: 18) obtained from the amyloid precursor protein sequence published by Yamada et al., *Biochem. Biophys. Res. Commun.*, 149:665–671 (1987). The cloned APP polynucleotide was then sequenced using the Sanger sequencing technique (See, i.e., *Proc. Nat'l. Acad. Sci.*, 74:5463–5467 (1989). The DNA band was separated on 1% agarose get in TAE buffer and cloned into pcDNA 3.1-eukaryote expression vector supplied by Invitrogen, Inc., as described below.

The nucleotide sequence of an amyloid precursor protein gene (APP695) is shown in FIG. 3, and appears in the sequence listing as SEQ ID NO:3. This sequence was shown to be 99% homologous with the APP695 from mouse (Yamada et al., *Biochem. Biophys. Res. Commun.*, 149:665–671 (1987)) and 90% homologous with human amyloid precursor protein (Robakis et al., *Proc. Natl. Acad. Sci.*, 84:4190–4194 (1987)). Careful analysis showed that changes in sequences are not at any vital regions of the molecule—such as within the AβP region—or the protein initiation site. The nucleotide substitutions appeared to be largely random, and not confined to any specific region of the molecule. Comparison of the amino acid sequences of APP695 in different species is shown in FIG. 4. APP695 for SAM-P8 mice is included in the sequence listing as SEQ ID NO:4; APP695 for Balb C mice as SEQ ID NO:5; rat as SEQ ID NO:6; monkey as SEQ ID NO:7; and human APP695 as SEQ ID NO:8. The results show that the APP695 protein is a highly conserved protein with an interesting difference being that the amino acid glycine at position 634 in Balb C mouse and human APP695 is replaced with asparagine in SAM-P8 mouse APP695.

EXAMPLE 2

This example illustrates cloning of APP cDNA into a eukaryotic expression vector and transfection into HeLa cells The purpose of this example was to demonstrate the regulation of mRNA to control the expression of a specific protein (AβP, in this case) by the use of antisense oligonucleotide technology. In order to develop effective molecular probes for the amyloid precursor protein synthesis system, APP cDNA was subcloned into a mammalian expression vector and expressed in HeLa cells. This system was used to show that amyloid precursor protein expression could be regulated with antisense oligonucleotides. In particular, a nucleotide, termed "OL-1" (SEQ ID NO: 1) was shown to effectively regulate amyloid precursor protein expression.

Materials:

Nitrocellulose paper was used for Western blotting. Luminol for chemiluminescent detection of proteins, and $^{35}$S-ATP were obtained from Amersham Radio Corporation, Arlington, Ill. X-Omat AR 50 X-ray film was obtained from Eastman Kodak Co., Rochester, N.Y. Agarose was obtained from Midwest Scientific, St. Louis, Mo. Mouse monoclonal anti-amyloid antibody, 6F3D, that recognized the amino acids downstream from the AβP region of amyloid precursor protein was obtained from DAKO Immunochemicals, Denmark. Buffers for electrophoresis and other chemicals, such as ethylenediaminetetraacetic acid disodium salt (EDTA), anti-rabbit IgG (whole molecule) and peroxidase conjugated second antibodies were obtained from Sigma Chemical Co., St. Louis, Mo. Reagents for PCR products were obtained from Perkin Elmer, San Diego, Calif. Lipofectamine was a product of Bethesda Research Laboratories, Md.

Cloning and Transfection of APP cDNA:

In order to express amyloid precursor protein in a eukaryotic system, amyloid precursor protein was cloned into pcDNA 3.1 provided by Invitrogen, Inc. using Xba I and Hind III sites for correct orientation. PCR product was generated using forward and reverse primers carrying these restriction sites at the amyloid precursor protein initiation and ternination sites. pcDNA 3.1 is a bacterial plasmid that carried the sequences needed for eukaryotic expression and for the ampicillin drug resistance gene. This was digested with Xba I and Hind III. The linearized plasmid was then treated with 20 units of calf intestinal phosphotase for 20 minutes at 37° C. to remove the self-ligating phosphate groups at their terminal ends. The plasmid was then purified by phenol-chloroform extraction and ethanol precipitation. The pcDNA 3.1 plasmid thus generated was ligated to the PCR product using $T_4$ ligase for 16 hrs at room temperature. The ligation mix was used to transform competent TNFα bacterial cells supplied by the Invitrogen Co. The transformed bacterial colonies were identified by plating the bacteria on ampicillin-containing LB-agar plates. A single bacterial colony carrying the APP cDNA was grown in LB-agar medium, the plasmid was isolated from the bacterial cells and sequenced to check for any possible errors introduced by PCR. After confirmation that no errors were present in the sequence, the plasmid was transfected into HeLa cells using lipofectamine. The cloned plasmid was referred to as pcDNA-AMT.

Transfection into HeLa cells was performed as described by Cui, et al., *J. Immunol.*, 151:4137–4146 (1993); and Colwell et al., *Biochem. Biophys. Acta*, 1172:175–180 (1993). Briefly, 30 μg of plasmid DNA was mixed with an equal volume of lipofectamine (from Bethesda Research Laboratories) and left at room temperature for 15 min. The mix was added to 5 ml of HeLa cells, 1×10$^6$ cells/ml, in RPMI without serum and incubated for 5 hrs at 37° C. The cells were then spun down at 2000×g and re-suspended in 5 ml of RPMI containing 10% fetal calf serum, and the cells were grown at 37° C. until use. Amyloid precursor protein specific transcription and translation was monitored by Northern blotting and Western blotting, respectively.

For Northern blotting, the total RNA obtained from the control and test samples was subjected to electrophoresis on 0.9% agarose gels under denaturing conditions as described by Kumar, *Biochem. Biophys. Res. Commun.*, 192:683–692 (1993). The RNA was transferred electrophoretically to a nitrocellulose paper. APP CDNA insert from the plasmid was excised by restriction digestion followed by electrophoresis on agarose gels. The purified insert was random prime labeled and used as a probe. Northern blots were subjected to hybridization in 6×SSC (standard saline citrate) in 1×Denhardt's for 72 hrs and exposed to X-ray film.

Expression of amyloid precursor protein or AβP protein was assessed by Western blot analysis. In this procedure, solubilized proteins were subjected to subjected to SDS-polyacrylamide gel electrophoresis (SDS-PAGE) on 10% polyacrylamide gels and Western blotted on to nitrocellulose papers using tris-glycine buffer and reacted with the primary antibody (see, e.g., Kumar et al., *Infect. Immun.*, 48:806–812 (1985)). The antigen-antibody complex was detected by the chemiluminescent technique.

HeLa cells from transfected and non-transfected culture flasks were homogenized in PBS (isotonic phosphate buffer, pH 7.4) containing 1% NP40, 2 mM PMSF, 1 μM pepstatin A, 3 mM EDTA and 3.7 mg/ml iodoacetamide. The samples were left on ice for 30 min and spun for 20 min at 20,000×g in a microcentrifuge. The crude supernatant was aspirated and protein content was estimated using a Biorad detergent compatible protein assay (Waterborg, J. H. and H. R. Matthews, *Methods Mol. Biol.*, 32:1–4 (1994)).

Figure 5:
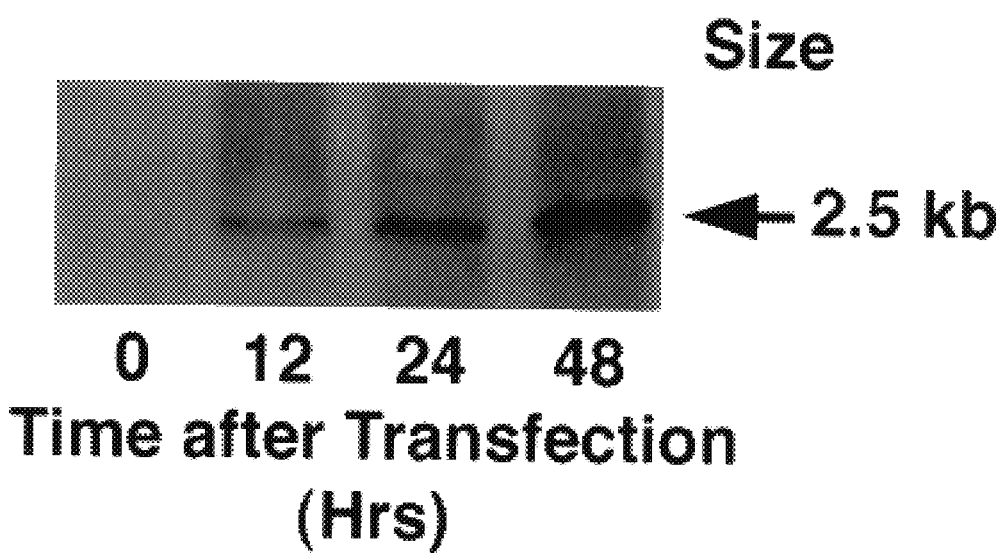
FIG. 5 is a Northern blot showing the increasing amount of amyloid precursor protein-specific RNA (APP mRNA) synthesized by APP cDNA transfected HeLa cells at 0, 12, 24 and 48 hours after transfection.

FIG. 5 shows a Northern blot of RNA obtained from the HeLa cell culture at various times after transfection. The results show that amyloid precursor protein-specific RNA could be detected within 12 hours after transfection and increased linearly up to about 48 hrs after transfection.

In order to study the effect of specific antisense oligonucleotides on amyloid precursor protein expression, three oligonucleotides; OL-1 (42 n-bases; SEQ ID NO: 1)—spanning amino acids 613–626; OL-2 (14 n-bases; SEQ ID NO:9)—spanning amino acids 613–618; and OL-3 (12 n-bases; SEQ ID NO:2)—spanning amino acids 618–621, of APP695, were synthesized.

Synthetic oligonucleotides complementary to amyloid precursor protein and the control antisense oligonucleotides were synthesized on an oligonucleotide synthesizer supplied by Beckman Instruments. The oligonucleotides were purified by polyacrylamide gel electrophoresis on 5% polyacrylamide gels. Phophorothionated antisense oligonucleotide OL-1 (SEQ ID NO: 1) that was HPLC purified was obtained from Midland Certified Reagents, Midland, Tex. Purity of the oligonucleotide was assessed by mass spectrometry.

In addition, two random oligonucleotides NSP-1 (10 n-bases; SEQ ID NO: 12); and NSP-2 (40 n-bases; SEQ ID NO:10), which exhibited less than 10% homology to any region in amyloid precursor protein were used as nonspecific controls.

Transfected cells were treated with various concentrations of nonspecific and antisense oligonucleotides by directly adding the oligonucleotides in an aqueous solution as described by Loke et al., *Proc. Natl. Acad. Sci., USA*, 86:3474–3478 (1989).

Figure 6:
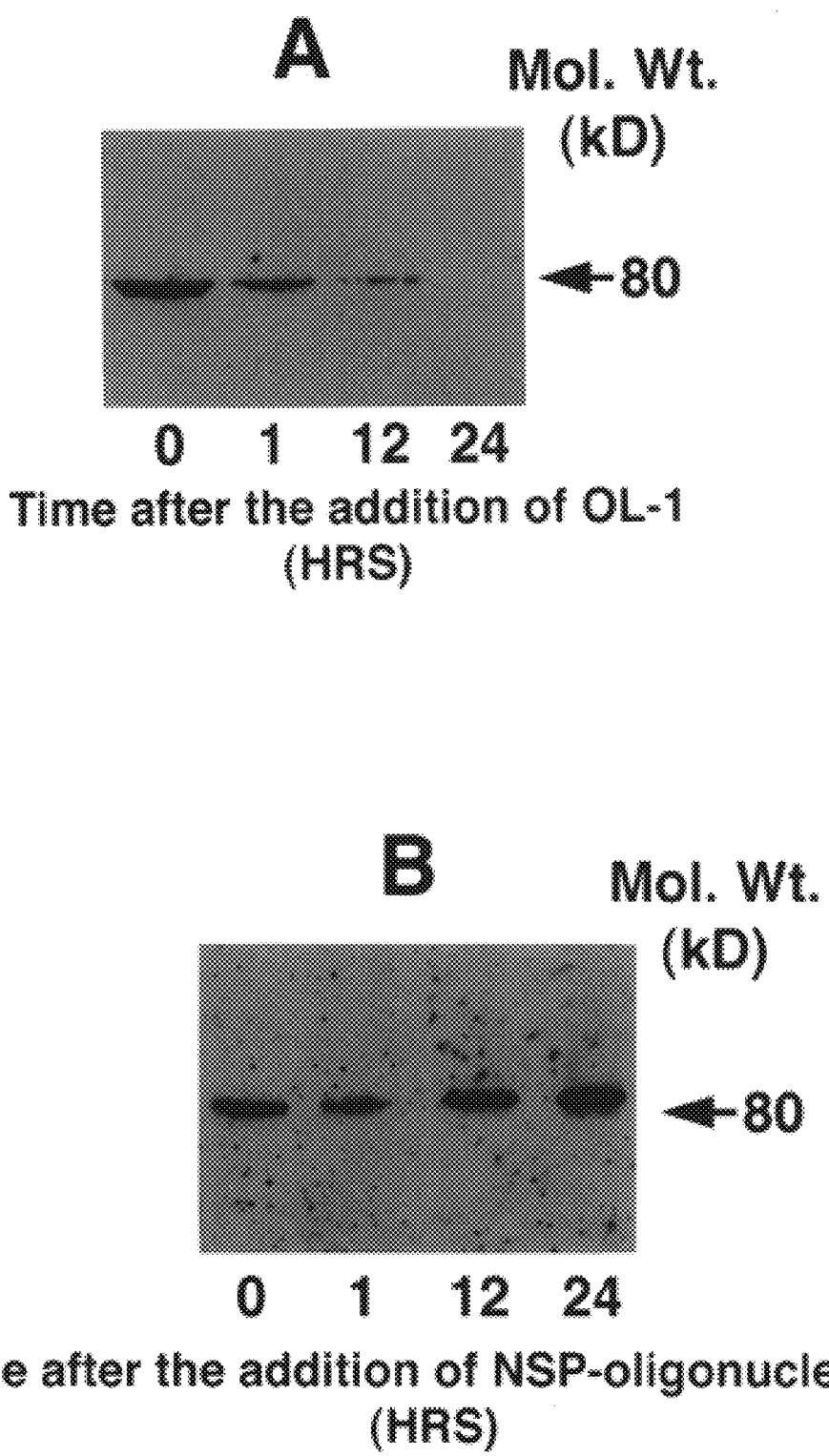
FIGS. 6(A–B) is a Western blot showing the inhibition of amyloid precursor protein expression in HeLa cells transfected with an APP-pcDNA 3.1 vector at 0, 1, 12 and 24 hours after treatment of the cells with 10 pmolar antisense oligonucleotide OL-1 (SEQ ID NO:1) (Panel A), or 10 pmolar random oligonucleotide NSP-1 (SEQ ID NO:12) (Panel B)

FIG. 6 shows the effect of OL-1 (SEQ ID NO: 1) on the synthesis of amyloid precursor protein as detected by Western blotting using monoclonal antibodies against amyloid precursor protein that recognize its C-terminal region. In this test, HeLa cells were transfected with pcDNA-AMT, and 24 hrs after transfection, the cells were treated with 10 pmoles (pico moles) of OL-1 (SEQ ID NO: 1). At 0, 1, 12 and 24 hours after transfection, the cells were harvested and amyloid precursor protein was measured by immunoblotting. The results shown in blot "A" indicate that the amount of amyloid precursor protein detected by the antibodies decreased over time until no amyloid precursor protein was detected at 24 hrs after the addition of OL-1 (SEQ ID NO:1). In contrast, blot "B" indicates that the administration of non-specific oligonucleotides NSP-1 (SEQ ID NO: 12) and NSP-2 (SEQ ID NO:10), had no effect on the expression of the C-terminal portion of amyloid precursor protein.

Figure 7:
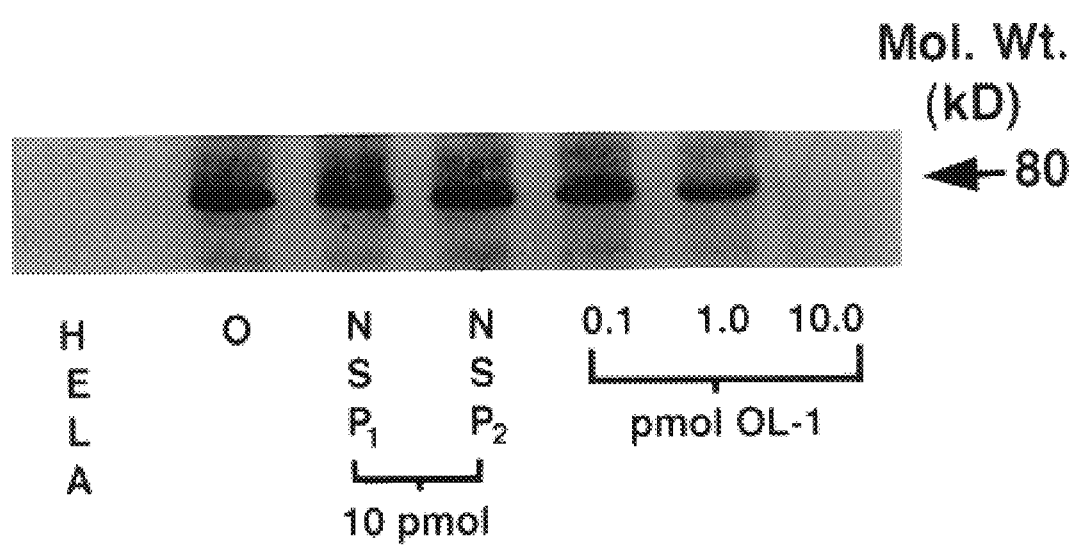
FIG. 7 is a Western blot that shows that the antibody used (6F3D) did not recognize amyloid precursor protein in non-transfected HeLa cells (lane marked "HELA"); contrasted with amyloid precursor protein expression by HeLa cells transfected with an APP-pcDNA 3.1 vector (lane 2, marked "O"); by transfected HeLa cells that had been treated with 10 pmoles of either NSP-I(SEQ ID NO: 12) or NSP-2 (SEQ ID NO: 10) (lanes marked NSP1 and NSP2, respectively); and with antisense oligonucleotide OL-1 (SEQ ID NO:1) at the specified three concentrations (lanes marked "0.1", "1" and "10")—where the concentrations were in pmoles.

FIG. 7 shows the effect of various concentrations of OL-1 (SEQ ID NO:1) on the expression of the C-terminal portion of amyloid precursor protein in HeLa cells. In this test, HeLa cells were transfected with cDNA-AMT and 24 hrs after transfection, either NSP-1, NSP-2 at 10 pmolar, or OL-1 (SEQ ID NO:1) at specified concentrations (0. 0.1, 1.0 and 10 pmolar) were added to the cells. At 24 hrs after the addition, the cells were harvested and tested for amyloid precursor protein expression by immunoblotting with C-terminal antibodies against amyloid precursor protein. The results indicated that the inhibition of expression of amyloid precursor protein is dependent upon the concentration of OL-1 (SEQ ID NO: 1). No amyloid precursor protein could be detected in the cells treated with 10 pmolar OL-1 (SEQ ID NO:1), but 0.1 pmolar and 1.0 pmolar concentrations of OL-1 (SEQ ID NO: 1) and 10 pmolar NSP-1 (SEQ ID NO:12) and NSP-2 (SEQ ID NO:10) showed no effect upon amyloid precursor protein expression.

In order to test the effect of OL-1 (SEQ ID NO:1) on the levels of amyloid precursor protein mRNA, HeLa cells transfected with pcDNA-AMT were treated with 10 pmoles of OL-1 (SEQ ID NO:1) and, at specified times, RNA was extracted and subjected to RNase protection assay.

For this test, a 140 bp fragment was generated by PCR using forward (5'ATCTCTGAAGTGAAGATG) SEQ ID NO:19 and reverse (5'GGTGATGACGATCACTGT) primers using the cloned APP cDNA. PCR reaction mixture contained 60 mM Tris-HCl, pH 8.8, 6 mM $MgCl_2$, 1 mM mercaptoethanol, 16 mM ammonium sulfate, 50 pm of forward and reverse primers and I mM each of the four deoxyribonucleotides. The sample was denatured at 94° C. for 5 min. and then subjected to 34 cycles of PCR of 1 min each at 55° C., 72° C., and 94° C. The product was gel purified and directly subcloned into a TA cloning vector obtained from Invitrogen, Inc., Carlsbad, CA. The plasmid was linearized and RNA was prepared using $T_7$ polymerase in the presence of radioactive CTP as described by Morley et al., *Life Sciences*, 57:1327–1331 (1995). The probe was then gel purified and 20,000 cpm was used for hybridization with 1 μg of total brain RNA using an RPA II kit supplied by Ambion Corporation, Austin, Tex. After hybridization, the hybrid was treated with RNase A and T1 and run on a 5% acrylamide gel.

The results, shown in FIG. 7, show that APP mRNA synthesis was not affected by OL-1 (SEQ ID NO:1) treatment.

Phosphorothionation of OL-1 (SEQ ID NO:1) did not change the pattern of inhibition of amyloid precursor protein expression. However, phosphorothionated OL-1 (SEQ ID NO:1) exhibited stability for a longer period of time. At concentrations as low as 1 pmole, amyloid precursor protein expression was suppressed if the cells were incubated for 48 hrs. Non-phosphorothionated OL-1 (SEQ ID NO:1) showed no effect on amyloid precursor protein expression at this concentration, suggesting that phosphorothionated OL-1 (SEQ ID NO: 1) is more stable than the normal oligonucleotide.

Discussion:

In this example, the molecular cloning, expression and specific inhibition of amyloid precursor protein from the SAM-P8 mouse hippocampus is reported. The selection of the P8 mouse was based on the fact that it loses cognitive abilities at a very early age and exhibits increased expression of amyloid precursor protein. Since AβP is known to be amnestic in mice, it is believed that a reduction in amyloid precursor protein expression may prove to be advantageous to overcome the early onset of cognitive differences. It has been shown that the injection of anti-amyloid precursor protein antibodies into the hippocampal region of these mice alleviate the learning disabilities (See, e.g., Flood and Morley, *Neuroscience and Behaviour*, 14:153–157 (1998)). In order to develop molecular probes, the use of antisense oligonucleotides was proposed to reduce amyloid precursor protein expression.

The SAM-P8 mouse brain specific APP cDNA was expressed in HeLa cells and it was shown that its expression could be regulated by an antisense oligonucleotide that was targeted against a specific sequence. The antisense oligonucleotide prevented the formation of AβP, while permitting the generation of at least a partial molecule of amyloid precursor protein (i.e., that portion of the amyloid precursor protein molecule that lay upstream of the target location for the antisense oligonucleotide). The OL-1 (SEQ ID NO:1) oligonucleotide, which showed such activity, spanned the α-secretase region of amyloid precursor protein and reduced amyloid precursor protein expression in a concentration and time-dependent manner. As no difference in amyloid precursor protein expression was observed with phosphorothionated oligonucleotides, the mechanism of inhibition by oligonucleotides appears to be other than RNase H cleavage of the message.

EXAMPLE 3

This example illustrates the efficacy of antisense oligonucleotides according to the present invention to improve acquisition and retention in 12-month-old SAM-P8 mice.

Figure 2:
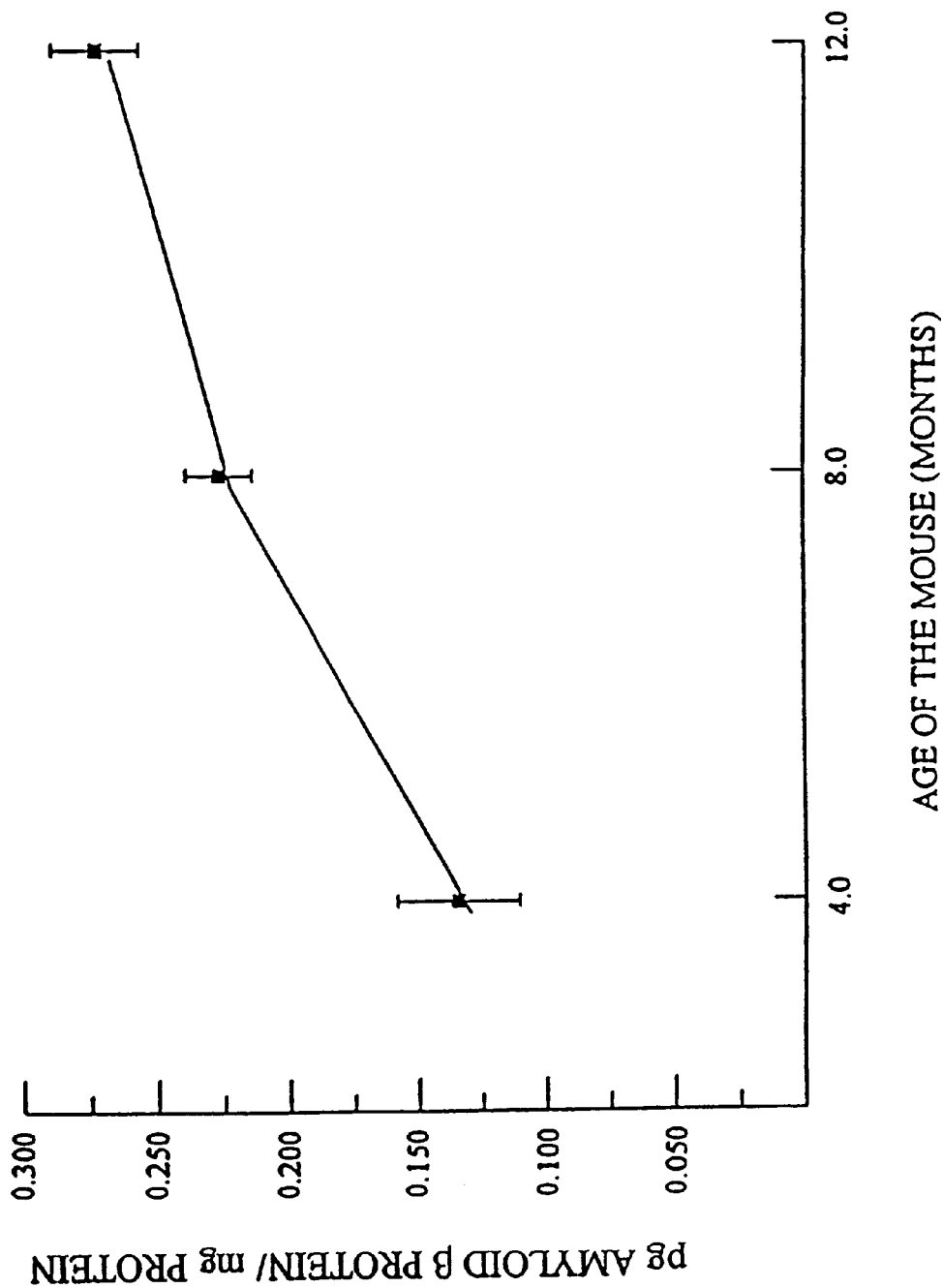
FIG. 2 shows a plot of the increasing amount of APP that was measured as being present in the brains of SAM-P8 mice at 4, 8 and 12 months of age.

Senescence accelerated mice (SAM) have been developed (Takeda et al., *Mech. Aging Dev.*, 17:183–184 (1981)), and one strain of such mice (the P8 strain) show an age-related increase in impaired learning (acquisition) and memory (retention) as well as an age-related increase in the accumulation of amyloid precursor protein and AβP. (Miyomoto et al., *Physiol. Behav.*, 38:399–409 (1986); and Flood, J. F. and J. E. Morley, *Neuroscience and Behavior*, 14:153–157 (1998)). SAM-P8 mice have a median life span of 17.2 months, as opposed to a normal life span of 24 months for standard R1 mice. The level of AβP was measured in the brains of SAM-P8 mice at 4, 8 and 12 months of age and is shown in FIG. 2. It is seen that the level of AβP rises steadily throughout the period.

Several similarities between Alzheimer's disease and some physiological manifestations of aging in SAM-P8 mice have been reported (Flood, J. F. and J. E. Morley, pp. 97–112, in *Memory Function and Aging Related Disorders*, Morley et al., Eds., Springer-Verlag Pul., NY (1992)). One of the manifestations is the increased expression of amyloid precursor protein with age in SAM-P8 mice. Mutations in amyloid precursor protein have been associated with increased expression of amyloid precursor protein and with familial Alzheimer's disease (FAD) (Goates et al, *Nature*, 349:704–706 (1991)). Thus, it can be inferred that either mutation(s) in amyloid precursor protein or over-expression of amyloid precursor protein could be one of the causes for the manifestation of loss of memory and acquisition in these mice.

Because the accumulation of AεP is one of the factors that contributes to the loss of cognitive ability early in the life of SAM-P8 mice, it was postulated that reducing its expression should have a favorable effect in preventing, or even reversing cognitive impairment. In order to test this hypothesis, several antisense oligonucleotides were designed that block the translation of different regions of amyloid precursor protein in the AβP region. The antisense oligonucleotides are labeled OL-1 (SEQ ID NO: 1) through OL-5 (SEQ ID NO:11), and their nucleic acid sequences are shown in Table 1, along with the corresponding targeted amino acids in amyloid precursor protein.

TABLE 1

Antisense and control random oligonucleotides used for inhibition of APP.

| NUMBER | SEQUENCE | CORRESPONDING AMINO ACIDS IN APP |
|---|---|---|
| OL-1 | GGCGCCTTTGTTCGAACCCACATCTTCAGCAA AGAACACCAG (SEQ ID NO:1) | LVFFAEDVGSNKGA (17–30 OF AβP) (SEQ ID NO:13) |
| OL-2 | GGCGCCTTTGTTCG (SEQ ID NO:9) | NKGA (27–30 OF AβP) (SEQ ID NO:15) |
| OL-3 | AACCCACATCTTCA (SEQ ID NO:2) | EDVG (22–25 OF AβP) (SEQ ID NO:14) |
| OL-4 | GATCACGTACACATCGACACCAGTCGCCATGA CTGAGCTT (SEQ ID NO:10) | Random-2 |
| OL-5 | TATGACAACGCCGCCCACCATGAGTCCGATGA TGGCGCCTTTGTT (SEQ ID NO:11) | NKGAHGLMVGGVVI (27–42 OF AβP) (SEQ ID NO:16) |

SAM-P8 mice were obtained from Dr. Takeda in Japan and maintained by Drs. Morley and Flood, at St. Louis University School of Medicine, St. Louis, Mo. The mice were divided into seven groups of 10 mice each. At 11 months of age (4 weeks prior to training) one group received 0.2 μl of calf serum by intracerebral ventricular injection (ICV), while the other six groups received one 0.2 μl injection ICV of an antibody specific for AβP (−AβP; obtained from DACO Industries). The purpose of the −AβP was to bind the AβP that was then in the brain. The antibody administration was performed by drilling a hole through the skull over the third ventricle (−0.5 relative to bregma; 0.5 mm right of central suture). The scalp was closed and the mice were returned to their cages. Two weeks after this first injection, one of the groups of −AβP-injected mice and the group that had received serum were injected with the saline vehicle that was used as the carrier for the antisense oligonucleotides. At this same time (two weeks before training), each one of the oligonucleotides listed in Table 1 was administered in saline ICV to all of the mice in one group. Each administration contained 0.2 μl and an amount of 60 ng of oligonucleotide per injection.

Figure 8:
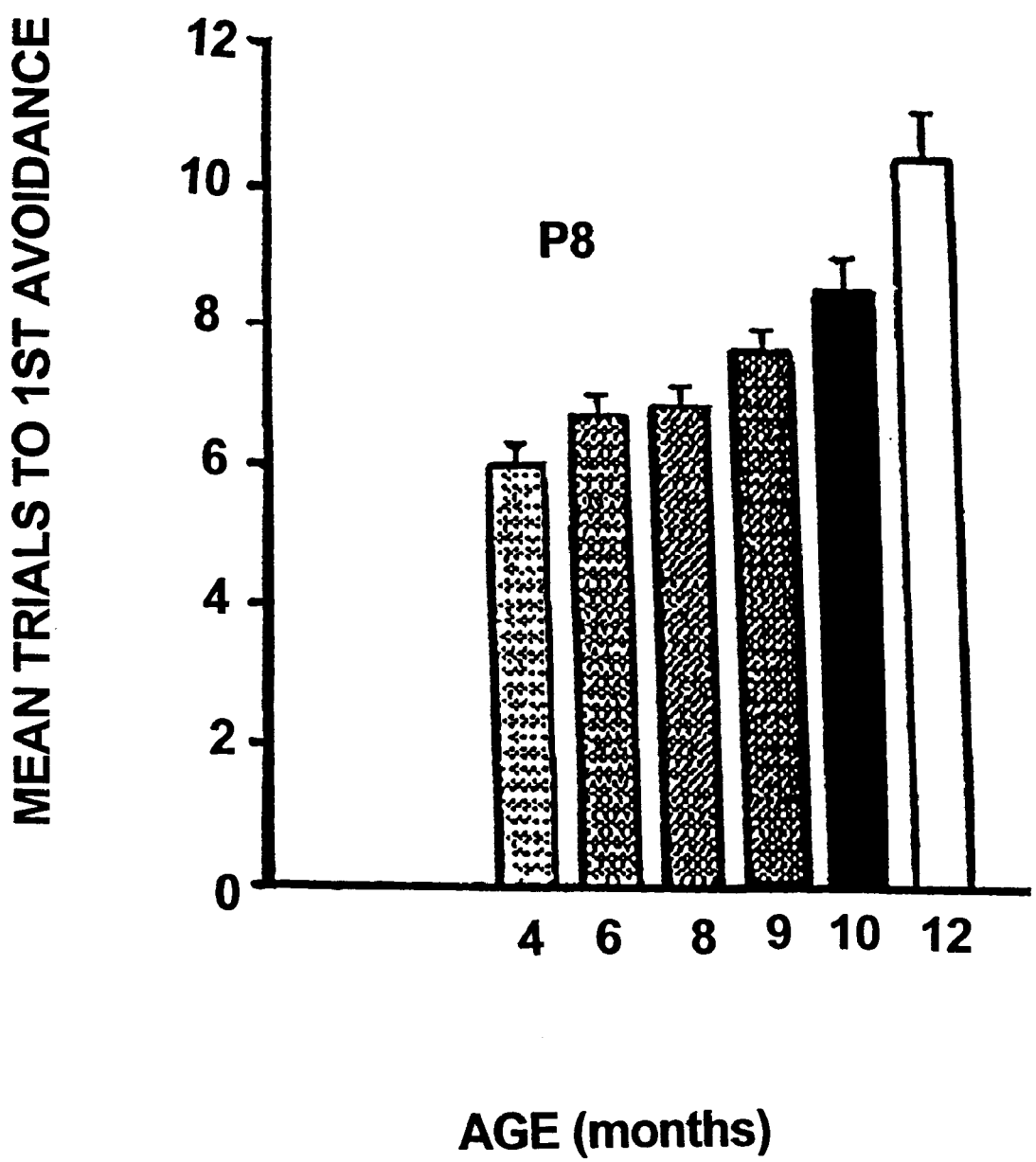
FIG. 8 shows the decreasing rate of acquisition by SAM-P8 mice, as shown by the increasing mean number of trials to the first avoidance of footshock, at 4, 6, 8, 9, 10 and 12 months of age.

Two weeks after the last injection, when the mice were 12 months of age, they were trained on footshock avoidance in a T-maze. The training and testing procedures were the same as described by Flood et al., *Physiology & Behavior*, 58:819–822 (1995); and Flood et al., *Neurobiology of Aging*, 14:159–166 (1993). The maze consisted of a black plastic start alley with a start box at one end and two goal boxes at the other end. A stainless steel rod floor ran throughout the maze. The start box was separated from the start alley by a plastic guillotine door that prevented the mouse from moving down the alley until the training started. The intertrial interval was 45 sec with a doorbell-type buzzer (65 dB) as the conditioned stimulus and a footshock intensity of 0.35 mA was administered by a Coulbourn Instruments scrambled grid floor shocker model E 13-08. A training trial began when a mouse was placed into the start box. The guillotine door was raised and the buzzer sounded simultaneously. After 5 sec, footshock was applied. The goal box the mouse first entered on the first trial was designated as "incorrect". Footshock was continued until the mouse entered the other goal box, which on all subsequent trials was designated "correct" for the particular mouse. At the end of each trial, the mouse was removed from the goal box and returned to its home cage. A new trial began by placing the mouse in the start box, sounding the buzzer and raising the guillotine door. Footshock was applied 5 sec later if the mouse did not leave the start box or failed to enter the correct goal box. All mice were trained until they made their first avoidance response. FIG. 8 shows the mean trials to first avoidance for 4-to-12 month-old SAM-P8 mice. A regular and significant increase in the number of trials to first avoidance is seen for these mice as they age, and their rate of acquisition at 12 months is much lower than at 4 months.

Training to the criterion of first avoidance was used to avoid "overtraining" and masking the effect of aging on long-term retention. With this criterion, both 4 and 12 month-old mice had good retention test scores when tested 1 hr after training. (See, e.g., Flood, J.F. and J. E. Morley, *Neurobiology of Aging*, 14: 153–157 (1993)). When tested one week later, 4 month-old P8 mice still had good retention, but 12 month-old mice had poor retention. (See, e.g., Flood, J. F. and J. E. Morley, *Neurobiology of Aging*, 14: 153–157 (1993); and Fox, S. W. and J. F. Flood, *Peptides*, 13:1079–1081 (1992)).

One week after original training, retention for both 4 and 12 month-old mice was tested by continuing the training until each mouse made 5 avoidances in 6 consecutive training trials. Results were expressed as means and with a standard error of the means. The trials to first avoidance, or to a criterion of 5 avoidances in 6 consecutive trials were analyzed in separate one way ANOVA's. Statistical differences between the means of the 12 month-old mice that received antisense oligonucleotides were compared to the means of the 12 month-old mice that received the saline solution vehicle using Dunnett's T-test. (See, e.g., Taffel et al., *Annals of the New York Academy of Sciences*, 678:293–305 (1993)). To test whether the groups that received antisense oligonucleotides differed significantly from the mean of the 4 month-old baseline groups Tukey's T-test was used.

Figure 9:
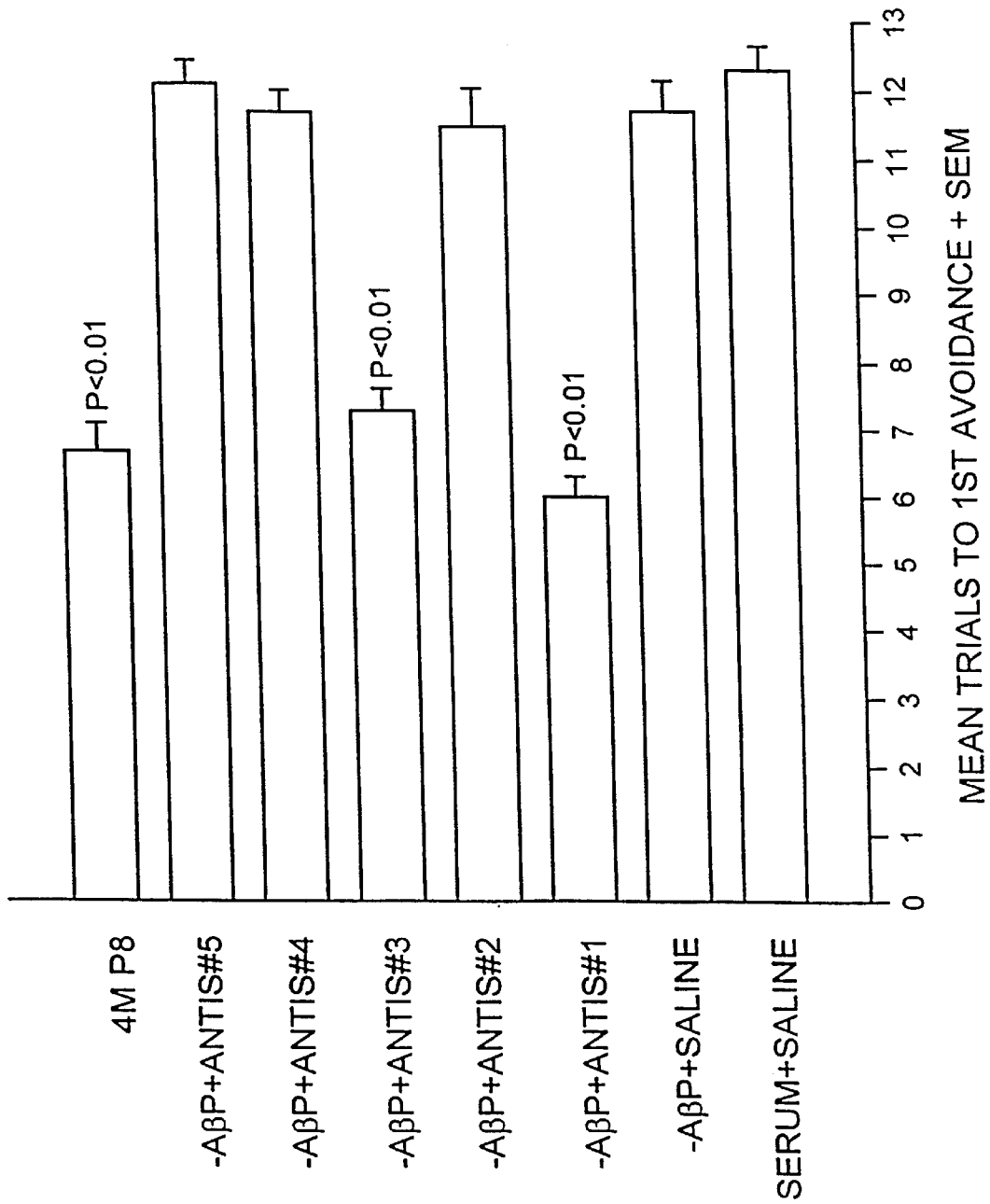
FIG. 9 shows the rate of acquisition by SAM-P8 mice, as measured by the mean number of trials to the first avoidance of footshock, for untreated 4 month-old mice (4MP8), and for 12 month-old mice treated ICV with one injection of either serum or AβP-specific antibody (–AβP) 4 weeks prior to training and then, at 2 weeks prior to training, with saline vehicle (Serum+Saline; and –AβP+Saline); or with antisense nucleotides OL-1 (SEQ ID NO:1) (–AβP+Antis#1); OL-2 (SEQ ID NO:9) (–AβP+Antis#2); OL-3 (SEQ ID NO:2) (–AβP+Antis#3); OL-4 (SEQ ID NO:10) (–AβP+Antis#4); or OL-5 (SEQ ID NO:11) (–AβP+Antis#5)

The data for acquisition (mean trials to first avoidance) for treated and untreated 12 month-old mice and for untreated 4 month-old mice are shown in FIG. 9. In this test, the lower the number of mean trial to first avoidance indicates better acquisition capability. It is seen that the groups given antisense oligonucleotides OL-1 (SEQ ID NO:1) (spanning AβP amino acids 17–30; i.e., amino acids 613–626 of APP695) and OL-3 (SEQ ID NO:2) (spanning AβP amino acids 22–25; i.e., amino acids 618–621 of APP695) were significantly lower at P<0.01 than the means of mice given the saline solution vehicle or random oligonucleotides. Furthermore, under similar conditions, antisense oligonucleotides OL-2 (SEQ ID NO:9) and OL-4 (SEQ ID NO: 10), which target binding sites on the amyloid precursor protein gene that are further downstream (toward the carboxyl-terminal of the molecule) than the target sites for OL-1(SEQ ID NO: 1) and OL-3 (SEQ ID NO:2), did not show any significant effect. In fact, it was seen that the acquisition of 12 month-old mice treated with OL-1 (SEQ ID NO: 1) was essentially the same as for untreated 4 month-old mice.

Figure 10:
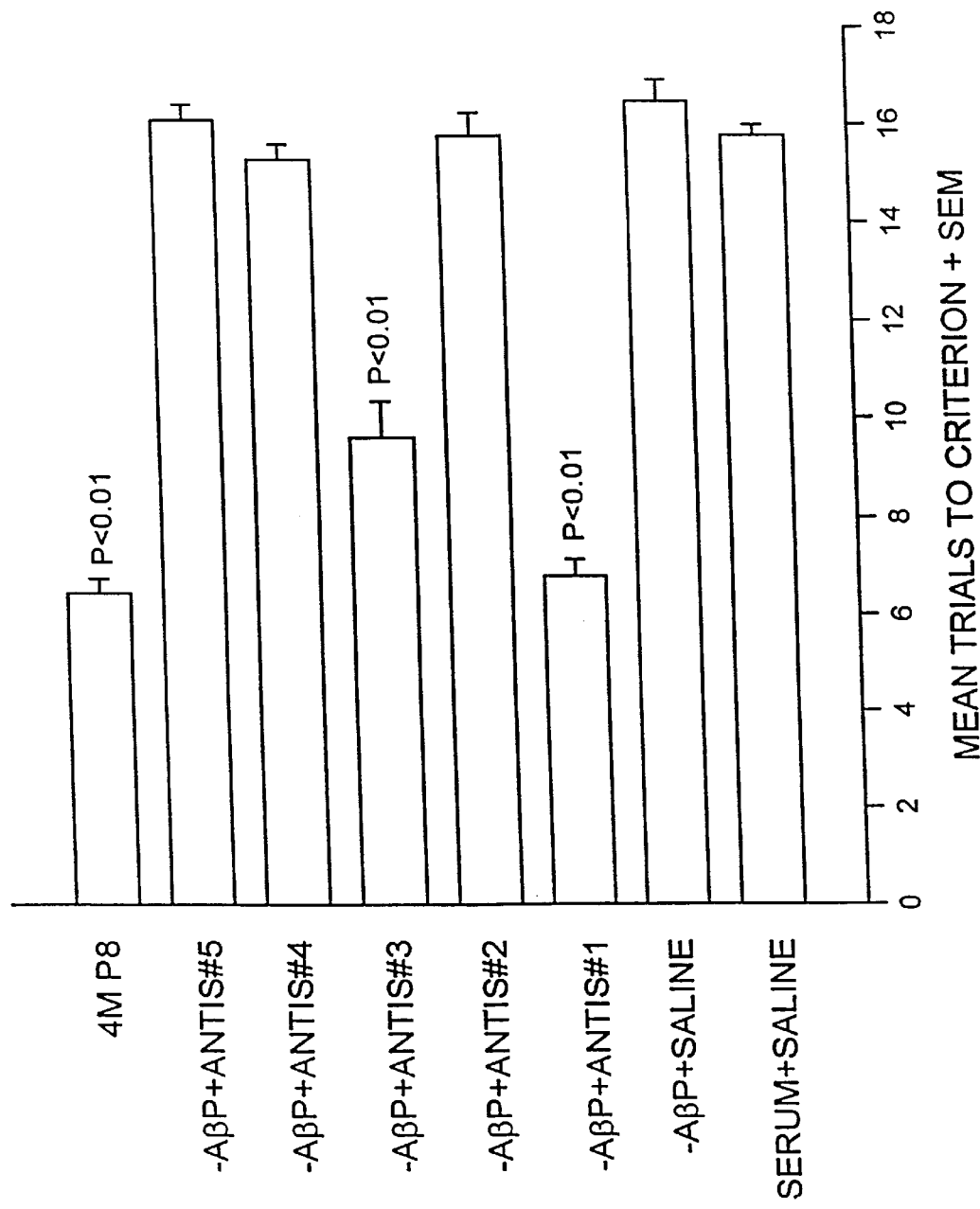
FIG. 10 shows retention for SAM-P8 mice, as measured by the mean number of trials to the criterion (5 avoidances out of 6 consecutive trials), for untreated 4 month-old mice (4MP8), and for 12 month-old mice treated ICV with one injection of either serum or APP-specific antibody (–AβP) 4 weeks prior to training and then, at 2 weeks prior to training, with saline vehicle (Serum+Saline; and –AβP+Saline); or with antisense nucleotides OL-1 (SEQ ID NO:1) (–AβP+Antis#1); OL-2 (SEQ ID NO:9) (–AβP+Antis#2); OL-3 (SEQ ID NO:2) (–AβP+Antis#3); OL-4 (SEQ ID NO:10) (–AβP+Antis#4); or OL-5 (SEQ ID NO:11) (–AβP+Antis#5)

The data for retention (five avoidances in six consecutive trials) for treated and untreated 12 month-old mice and for untreated 4 month-old mice are shown in FIG. 10. Here again, the lower the mean number of trials required for the mice to demonstrate five avoidances in six consecutive trials, the better their retention capability. And, as with the acquisition data, it is seen that the retention capability of the mice in groups given antisense oligonucleotides OL-1 (SEQ ID NO:1) (spanning AβP amino acids 17–30; i.e., amino acids 613–626 of APP695) and OL-3 (SEQ ID NO:2) (spanning AβP amino acids 22–25; i.e., amino acids 618–621 of APP695) was significantly lower (therefore better) at P<0.01 than the retention capability of mice given the saline solution vehicle or random oligonucleotides. Furthermore, under similar conditions, antisense oligonucleotides OL-2 (SEQ ID NO:9) and OL-4 (SEQ ID NO: 10) did not show any significant effect. And, as with acquisition, it was seen that the retention capability of 12 month-old SAM P8 mice treated with OL-1(SEQ ID NO:1) was essentially the same as for untreated 4 month-old mice.

Samples were recovered from the amygdala (A), hippocampal (H) and septum (S) regions of the brains of each of four mice, two of which had been treated with the saline vehicle (S) and the other two of which had received the antisense oligonucleotides (A). Thus, for example, a sample recovered from the amygdala of a mouse that had received saline in the test was designated AS. The samples were tested for amyloid precursor protein expression by immunoblotting against an antibody that specifically hybridizes to the C-terminal portion of the amyloid precursor protein. The results, shown in FIG. 11, track A, indicate that there was a significant reduction in amyloid precursor protein in the brain samples of mice that had received the antisense oligonucleotide, but no reduction of amyloid precursor protein in the brain samples of mice that received saline. Track B, of FIG. 11, shows that there was no reduction in the levels of APP mRNA in any of the samples taken (when tested by an RNase protection assay). These results are in agreement with the observation that increased AβP is involved in the pathogenesis of the cognitive defects in P8 mice. Furthermore, the results suggest that the N-terminal portion of AβP may play an important role in the generation of cognitive defects. The antisense oligonucleotides that block the synthesis of amyloid precursor protein beyond amino acid 27 of AβP (corresponding to amino acid 623 of APP695) do not seem to play an important role in affecting cognitive deficits. However, some antisense oligonucleotides that blocked amyloid precursor protein synthesis within the AβP region, but upstream of amino acid 25 of AβP (corresponding to amino acid 621 of APP695), apparently reversed the acquisition impairment in SAM-P8 mice.

Mechanistically, it appears that under normal conditions AβP is produced rapidly and cleared equally rapidly. If the clearance is slowed down, either due to aging or by impaired clearing mechanisms, the residual deposits of amyloid participate in causing memory deficits. Thus, reduction in amyloid precursor protein translation at locations specific for memory impairment by antisense oligonucleotides seems to compensate for the reduced clearance of AβP, thus helping to restore the memory deficit induced by aging.

EXAMPLE 4

This example illustrates the efficacy of administering the antisense oligonucleotides by intravenous injection.

In order to determine whether antisense oligonucleotide OL-1 (SEQ ID NO: 1) could successfully cross the blood-brain barrier if injected intravenously, the antisense oligonucleotide was labeled with $^{32}$P-γ-ATP using $T_4$ polynucleotide kinase. The labeled antisense oligonucleotide was purified by Sephadex spin column followed by ethanol precipitation. The purity of the oligonucleotide was verified by polyacrylamide gel electrophoresis.

The purified antisense oligonucleotide was injected into mice intravenously through the tail vein. At different time periods after the injection (from 10 min to 2 hrs), the animals were sacrificed and the distribution of radioactivity in various tissues was measured by counting the radioactivity in tissue extracts in a Beckman scintillation counter. In addition, the tissue extracts were run on polyacrylamide gels to assess the stability of the nucleotide.

The results showed that while the majority of the radioactivity was present in the liver, from 1% to 2% was observed in the brain. In all the tissues tested, including brain, the oligonucleotide showed little or no degradation. It was found that injection of the antisense oligonucleotide intravenously (IV) provided the same results as administration of the antibody by ICV (injection directly into the brain).

EXAMPLE 5

This example shows the efficacy of different regimens of treatment using the antisense oligonucleotides.

The experiment described in Example 3 was repeated, except that the injection of anti-AβP antibody (–AβP) was replaced by an injection of the antisense oligonucleotide. It was found that two injections (each of 2 μl and having 60 ng of oligonucleotide) of the antisense oligonucleotide within two weeks—rather than one injection of the –AβP antibody followed by one injection of the antisense oligonucleotide—provided the same results as administration of the antibody followed by the antisense oligonucleotide as shown in Example 3.

All references, including without limitation all papers, publications, presentations, texts, reports, manuscripts, brochures, pamphlets, internet postings, journal articles, periodicals, dictionaries, and the like, cited in this specification are hereby incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. An antisense compound comprising a nucleic acid sequence complementary to a nucleic acid sequence that encodes the amino acids of an amyloid precursor protein corresponding to amino acids 618–621 of SEQ ID NO:4 and which inhibits the expression of an amyloid beta protein (AβP) portion of the amyloid precursor protein coding sequence while permitting the expression of at least a portion of the amyloid precursor protein polynucleotide 5' to the AβP portion of the amyloid precursor protein sequence.

2. The antisense compound set forth in claim 1, wherein the expressed portion of the amyloid precursor protein polynucleotide 5' to the AβP portion of the amyloid precursor protein coding sequence comprises at least 20 nucleotides.

3. The antisense compound set forth in claim 2, wherein the expressed portion of the amyloid precursor protein polynucleotide 5' to the AβP portion of the amyloid precursor protein coding sequence comprises at least 200 nucleotides.

4. The antisense compound set forth in claim 3, wherein the expressed portion of the amyloid precursor protein polynucleotide 5' to the AβP portion of the amyloid precursor protein coding sequence comprises the entire portion of the amyloid precursor protein coding sequence 5' to the AβP portion of the amyloid precursor protein coding sequence.

5. The antisense compound as set forth in claim 1, wherein the antisense compound comprises at least 12 nucleotides.

6. The antisense compound set forth in claim 1, wherein the sequence coding for amyloid precursor protein comprises SEQ ID NO:3.

7. The antisense compound as set forth in claim 5, wherein the antisense compound comprises at least 12 nucleotides of SEQ ID NO:1 or SEQ ID NO:2.

8. The antisense compound set forth in claim 7, wherein the antisense compound consists of SEQ ID NO: 1.

9. The antisense compound set forth in claim 7, wherein the antisense compound consists of SEQ ID NO:2.

10. The antisense compound set forth in claim 2, wherein the antisense compound is an antisense oligonucleotide.

11. The antisense oligonucleotide set forth in claim 10, wherein the antisense oligonucleotide is targeted to that portion of amyloid precursor protein nucleotide sequence that encodes amino acids 22–25 of AβP (SEQ ID NO:14).

12. The antisense compound set forth in claim 1, which comprises at least one modified internucleoside linkage.

13. The antisense compound set forth in claim 12, wherein the modified linkage is a phosphorothioate linkage.

14. The antisense compound set forth in claim 1, which comprises at least one modified sugar moiety.

15. The antisense compound set forth in claim 14, wherein the modified sugar moiety is a 2'-O-methoxyethyl sugar moiety.

16. The antisense compound set forth in claim 1, which comprises at least one modified nucleobase.

17. The antisense compound set forth in claim 16, wherein the modified nucleobase is a 5-methylcytosine.

18. A pharmaceutical composition comprising the antisense compound of claim 1 and an excipient.

19. The pharmaceutical composition as set forth in claim 18, wherein the antisense compound comprises at least 12 nucleotides of SEQ ID NO:1 or SEQ ID NO:2.

20. The pharmaceutical composition as set forth in claim 19, wherein the antisense compound consists of SEQ ID NO: 1.

21. The pharmaceutical composition as set forth in claim 19, wherein the antisense compound consists of SEQ ID NO:2.

22. The composition as set forth in claim 19, wherein the excipient is saline solution.

23. The composition as set forth in claim 7, further comprising a substance which promotes penetration or transport of said compound across the blood-brain barrier.

24. The composition as set forth in claim 23, wherein the antisense compound is coupled to a viral vector.

25. A recombinant DNA or RNA molecule having a DNA or RNA sequence which, upon transcription, produces an antisense RNA against a nucleic acid encoding an amyloid beta protein, said antisense RNA comprising a nucleic acid segment which specifically hybridizes to the complement of one of the nucleic acid molecules of SEQ ID NO:1 or SEQ ID NO:2.

* * * * *

UNITED STATES PATENT AND TRADEMARK OFFICE
CERTIFICATE OF CORRECTION

PATENT NO. : 6,310,048 B1
DATED : October 30, 2001
INVENTOR(S) : Kumar

Page 1 of 1

It is certified that error appears in the above-identified patent and that said Letters Patent is hereby corrected as shown below:

<u>Title page,</u>
Item [73], Inventor, replace "Vijaya B. Kumar, Ellisville, MO (US)" with
-- Vijaya B. Kumar, Ellisville, MO (US)
   James F. Flood, II, St. Louis, MO (US)
   John E. Morley, St. Louis, MO (US) --

Signed and Sealed this

Nineteenth Day of March, 2002

Attest:

*Attesting Officer*

JAMES E. ROGAN
*Director of the United States Patent and Trademark Office*